(12) United States Patent
Dermody et al.

(10) Patent No.: US 8,293,498 B2
(45) Date of Patent: Oct. 23, 2012

(54) SYSTEM FOR GENERATION OF VIABLE REOVIRUS FROM CLONED CDNA

(75) Inventors: Terence S. Dermody, Brentwood, TN (US); Takeshi Kobayashi, Kyoto (JP); James D. Chappell, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1325 days.

(21) Appl. No.: 11/960,357

(22) Filed: Dec. 19, 2007

(65) Prior Publication Data

US 2012/0142078 A1      Jun. 7, 2012

Related U.S. Application Data

(60) Provisional application No. 60/871,058, filed on Dec. 20, 2006.

(51) Int. Cl.
*C12N 7/02* (2006.01)
*C12N 7/01* (2006.01)
*C12N 7/00* (2006.01)

(52) U.S. Cl. ............. 435/69.1; 435/235.1; 435/239

(58) Field of Classification Search ............ None
See application file for complete search history.

(56) References Cited

U.S. PATENT DOCUMENTS 6,703,232 B2      3/2004     Thompson et al. ......... 435/235.1

OTHER PUBLICATIONS

Boot et al., "Efficient rescue of infectious bursal disease virus from cloned cDNA: evidence for involvement of the 3'-terminal sequence in genome replication," *Virology*, 265:330-341, 1999.
Carvalho et al., "Silencing and complementation of reovirus core protein mu2: functional correlations with mu2-microtubule association and differences between virus- and plasmid-derived mu2," *Viorlogy*, 364:301-316, 2007.
Chandran et al., "Complete in vitro assembly of the reovirus outer capsid produces highly infectious particles suitable for genetic studies of the receptor-binding protein," *J. Virol.*, 75:5335-5342, 2001.
Kobayashi et al., "A plasmid-based reverse genetics system for animal double-stranded RNA viruses," *Cell Host & Microbe*, 1:147-157, 2007.
Kobayashi et al., "Gene-specific inhibition of reovirus replication by RNA interference," *J. Virol.*, 80:9053-9063, 2006.
Komoto et al., "Reverse genetics system for introduction of site-specific mutations into the double-stranded RNA genome of infectious rotavirus," *PNAS*, 103:4646-4651, 2006.
Roner and Steele, "Localizing the reovirus packaging signals using an engineered m1 and s2 ssRNA," *Virology*, 358:89-97, 2007.
Roner et al., "Construction and characterization of a reovirus double temperature-sensitive mutant," *PNAS*, 94:6826-6830, 1997.
Roner, "Reovirus RNA is infectious," *Virology*, 179:845-852, 1990.

*Primary Examiner* — Robert A Zeman
(74) *Attorney, Agent, or Firm* — Parker Highlander PLLC

(57) ABSTRACT

The present invention provides methods for the generation of viable reoviruses using only cloned nucleic acid segments representing the RNA segments of the reovirus genome.

16 Claims, 12 Drawing Sheets

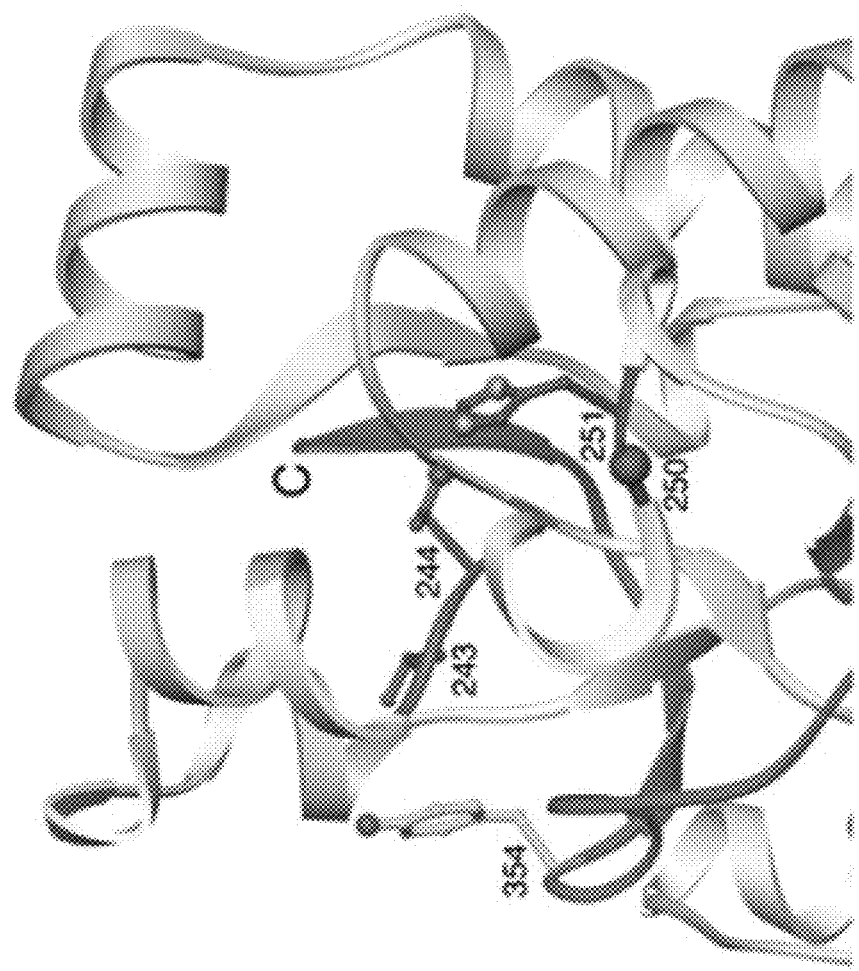
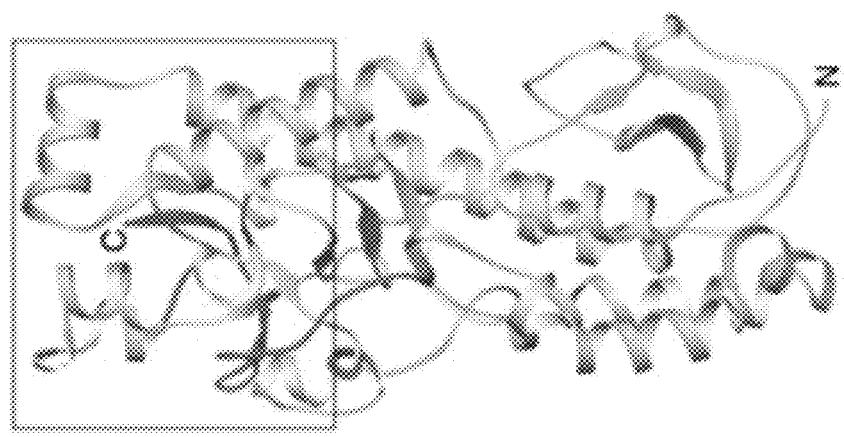
FIG. 5

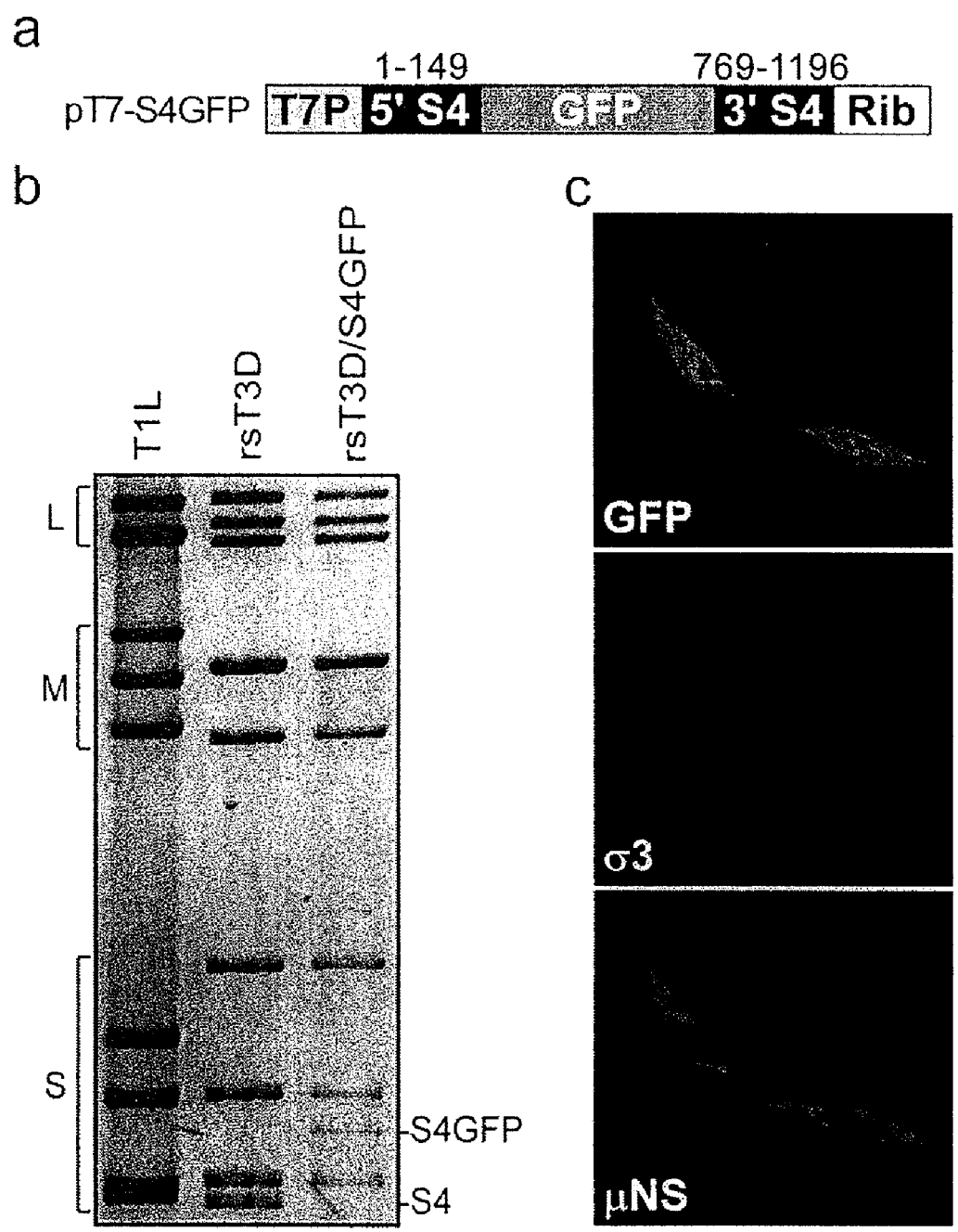
FIG. 6A-C

A
B
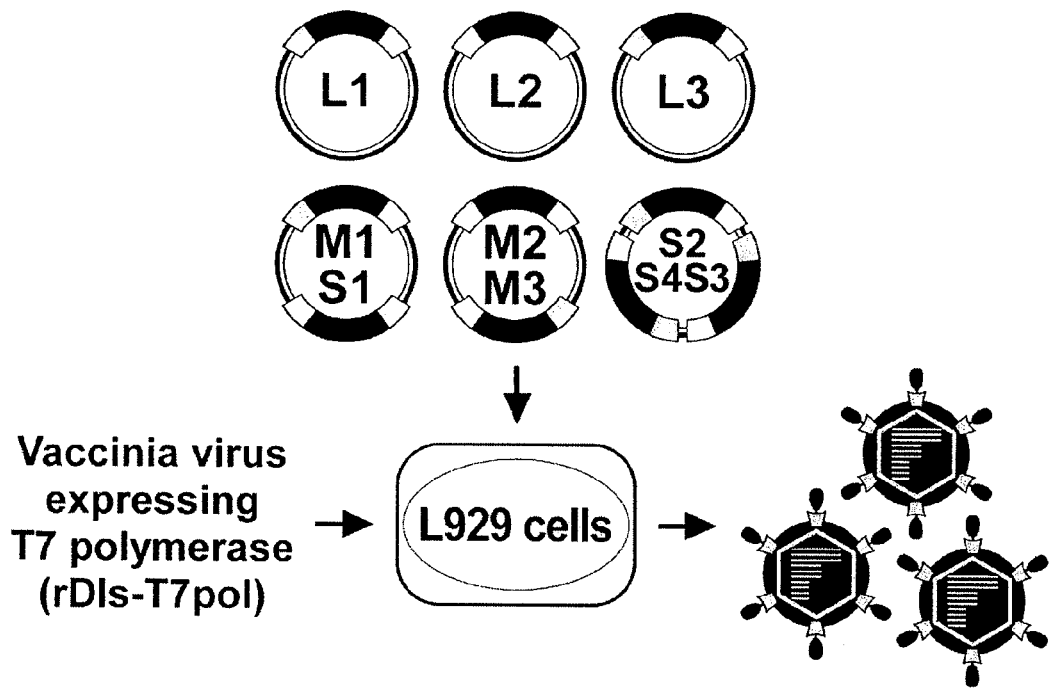
FIG. 7A-B

SYSTEM FOR GENERATION OF VIABLE REOVIRUS FROM CLONED CDNA

The present application claims benefit of priority to U.S. Provisional Application Ser. No. 60/871,058, filed Dec. 20, 2006, the entire contents of which are hereby incorporated by reference.

The invention was made with government support under grant numbers R01 AI32539 and R37 AI38296 awarded by the National Institute of Allergy and Infectious Diseases. The government has certain rights in the invention.

BACKGROUND OF THE INVENTION

1. Field of the Invention

The present invention relates generally to the fields of microbiology, molecular biology and virology. More particularly, it concerns methods of generating infectious reovirus containing selected modifications using cloned DNA.

2. Description of Related Art

Mammalian orthoreoviruses (reoviruses) are members of the Reoviridae family. Reoviruses contain 10 double-stranded (ds) RNA gene segments enclosed in two concentric protein shells, outer capsid and core (Nibert and Schiff, 2001). These viruses serve as a versatile experimental system for studies of viral replication events at the virus-cell interface, including engagement of cell-surface receptors (Barton et al., 2001a), internalization and disassembly (Ebert et al., 2002; Ehrlich et al., 2004), and activation of the innate immune response, including NF-κB-dependent cellular signaling pathways (Connolly et al., 2000; O'Donnell et al., 2006). Reoviruses also provide a model system for studies of virus-induced apoptosis and organ-specific disease in vivo (O'Donnell et al., 2005).

With the exception of dsRNA viruses, a reverse genetics system exists for all major groups of animal RNA viruses, including picornaviruses (Racaniello and Baltimore, 1981), rhabdoviruses (Schnell et al., 1994; Lawson et al., 1995; Whelan et al., 1995) paramyxoviruses (Collins et al., 1995; Garcin et al., 1995; Yoneda et al., 2006), bornaviruses (Schneider et al., 2005), flaviviruses (Rice et al., 1989; Gritsun and Gould, 1995; Kinney et al., 1997; Yun et al., 2003), bunyaviruses (Bridgen and Elliott, 1996), orthomyxoviruses (Fodor et al., 1999; Neumann et al., 1999), and coronaviruses (Almazan et al., 2000; Yount et al., 2003; Coley et al., 2005). Notably, viral genome structure does not appear to dictate the potential for plasmid-based virus recovery since monopartite and segmented RNA viruses of both positive and negative polarity have been generated by reverse genetics methods. As positive-strand virus genomic RNA is competent for translation, productive viral infections have been initiated by transfection of cells with plasmids that express full-length viral mRNA or, more commonly, with viral RNA transcribed in vitro from cDNA templates. In contrast, genomic RNA of negative-strand viruses is incapable of autonomous replication and requires coexpression of viral replication proteins to reconstitute functional replication complexes on full-length viral antigenomic or genomic RNA transcribed from transfected plasmids by bacteriophage or cellular RNA polymerase.

Despite extensive efforts in several laboratories, generation of an animal dsRNA virus entirely from cloned cDNAs has not been achieved. This critical technological gap is perhaps the single most important limitation to studies of these viruses. Previous work on reovirus and rotavirus reverse genetics has resulted in entirely RNA-based (Roner et al., 1997) or partially plasmid-based (Komoto et al., 2006) systems that permit replacement of one or two viral genes. These approaches have been used to rescue temperature-sensitive reovirus strains (Roner et al., 1997), define packaging signals in reovirus RNAs (Roner and Steele, 2006), and isolate rotaviruses containing engineered changes in the viral attachment protein (Komoto et al., 2006). However, neither the reovirus nor rotavirus reverse genetics systems in their current configurations permit selective introduction and recovery of desired mutations in each viral gene segment.

SUMMARY OF THE INVENTION

Thus, in accordance with the present invention, there is provided a method of generating an infectious Reoviridae particle comprising (a) providing cDNAs corresponding to each viral RNA transcript, each of said cDNAs being under the control of an RNA polymerase promoter; (b) transferring each of said cDNAs into a host cell that expresses said RNA polymerase that directs transcription from said promoter; and (c) culturing said host cell under conditions supporting production of a Reoviridae particle. The method may further comprise isolating said Reoviridae particle. Step (b) may comprise lipofection, calcium phosphate precipitation, or electroporation. The cDNAs may be comprised within plasmids.

The Reoviridae particle may be from the genus Orthoreovirus, Orbivirus, Rotavirus, Coltivirus, Seadornavirus, Aquareovirus, Cypovirus, Fijivirus, Phytoreovirus, Oryzavirus, or Mycoreovirus. The Reoviridae particle may be a reovirus particle, and said RNA polymerase is a bacterial T7 RNA polymerase. The cDNA(s) in step (a) may contain a mutation relative to the wild-type strain of virus from which the cDNA was synthesized, including 2, 3, 4, 5, 6, 7, 8, 9, 10, 11 or 12 of said cDNAs containing a mutation relative to the wild-type strain of virus from which the cDNA was synthesized. The mutation may alter the cell tropism of the generated Reoviridae particle. The cDNA(s) in step (a) may contain a heterologous nucleic acid segment, such as one encoding a heterologous polypeptide, including a vaccine antigen, a single-chain antibody, a tumor suppressor, an inducer or suppressor of apoptosis, a growth factor, a cytokine, an antisense molecule, a ribozyme, an interfering RNA, a fluorescent polypeptide, a luminescent polypeptide, or a dye-binding polypeptide.

The host cell may comprise a genomic DNA sequence expressing said RNA polymerase. The host cell may comprise an episomal nucleic acid sequence expressing said RNA polymerase, such as a viral expression construct, including a vaccinia viral expression construct. The host cell may be a 293T cell, 3T3 cell, Chinese hamster ovary cell, HeLa cell, L929 cell, murine embryonic fibroblast cell, murine erythroleukemia cell, Vero cell, CV-1 cell, or HT1080 cell.

Multiple cDNAs may be under the control of a single promoter, and may be separated by internal ribosome entry sites. Two, 3 or 4 cDNAs may be expressed within a single plasmid vector under the control of individual promoters or each under the control of a single promoter, and all of said cDNAs may be comprised in as few as 6, 7, 8, 9 or 10 plasmids.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." "About" means plus or minus 5% of the stated value.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Prototype reovirus gene segment cDNA in plasmid. Cloned cDNAs representing each of the 10 full-length reovirus RNA gene segments are flanked by the bacteriophage T7 RNA polymerase promoter (T7P) and the antigenomic hepatitis delta virus (HDV) ribozyme (Rib). (FIG. 1B) Schematic of approach. The ten reovirus cDNA constructs are transfected into murine L cells expressing T7 RNA polymerase from recombinant vaccinia virus strain rDIs-T7pol, which is replication defective. Nascent transcripts correspond to viral mRNAs containing the native 5' end. Self cleavage by the HDV ribozyme generates the native viral 3' end. Following 5 d of incubation, transfected cells are lysed by freeze-thaw, and viable viruses rescued from cloned cDNAs are isolated by plaque assay using L cells. (FIG. 1C) Kinetics of virus production following plasmid transfection of L cells. Cells were transfected with plasmid DNA according to the protocol in FIG. 1B and lysed at the intervals shown. Viral titers in cell lysates were determined by plaque assay.

(FIG. 2A) Electropherotypes of T1L, T3D, rsT3D, and rsT3D/T1LS1. Viral dsRNA was extracted from purified virions and electrophoresed in an SDS-polyacrylamide gel, followed by ethidium bromide staining to visualize viral gene segments. Size classes of gene segments (L, M, S) are indicated. (FIG. 2B) Recombinant viruses contain a novel mutation in the L1 gene (SEQ ID NOS:1-4). The single nucleotide difference in L1 unique to rsT3D and rsT3D/T1LS1 is shown in the alignment. The G→A substitution at position 2205 is a signature change engineered into the cloned T3D L1 cDNA used for marker rescue. (FIG. 2C) Sequence analysis of L1-gene RT-PCR products from rescued reoviruses. A fragment of the L1 gene was amplified by one-step RT-PCR performed using viral dsRNA extracted from purified virions of T3D, rsT3D, and rsT3D/T1LS1. Products were subjected to direct sequence analysis and compared to the L1 sequence of T3D. Shown are sequence chromatograms demonstrating G→A substitution at position 2205 of the rsT3D and rsT3D/T1LS1 L1 genes. (FIG. 2D) Immunofluorescence of cells infected with T3D and rsT3D. L cells were mock-infected or infected with either T3D or rsT3D and stained at 18 h post-infection with anti-μNS antiserum to visualize reovirus inclusions (green) and TO-PROS to visualize nuclei (blue). Representative digital fluorescence (top panel) and DIC images (bottom panel) for mock-, T3D-, and rsT3D-infected cells are shown. Scale bars, 10 μM. (FIG. 2E) One-step growth curve for T1L, T3D, rsT3D, and rsT3D/T1LS1 in L cells (left) and MEL cells (right). Cells were infected with virus, incubated for the intervals shown, and lysed by freeze-thaw. Viral titers in cell lysates were determined by plaque assay. The results are presented as the mean viral titers for triplicate experiments. Error bars indicate SD.

(FIG. 3A) Model of σ1 generated by adding five β-spiral repeats to the N-terminus of the crystallized σ1 fragment (Chappell et al., 2002). The three monomers of the crystallized fragment are shown in red, yellow, and blue; the model is shown in grey. The inset shows an enlarged view of the β-spiral region in σ1 that influences susceptibility of the molecule to cleavage by intestinal proteases (Chappell et al., 1998). Side chains of Arg245 and Thr249 are depicted in ball-and-stick representation. (FIG. 3B) Electrophoretic analysis of viral structural proteins of rsT3D and rsT3D-σ1T249I during treatment with trypsin to generate ISVPs. Purified $^{35}$S-methionine-labeled virions were treated with trypsin for the indicated intervals and loaded into wells of 4-20% polyacrylamide gradient gels. After electrophoresis, gels were prepared for fluorography and exposed to film. Samples of untreated virions appear in the lanes labeled V. Viral proteins are labeled. Positions of molecular weight standards (in kDa) are indicated. Images were cropped and processed using the auto-contrast feature of Adobe Photoshop. The experiments shown are representative of two performed for each virus. (FIG. 3C) Infectivity of rsT3D and rsT3D-σ1T249I during treatment with trypsin to generate ISVPs. Purified virions were treated with trypsin at 37° C. for the specified intervals. Titers of virus in the treatment mixtures were determined by plaque assay. The results are presented as the mean viral titers for triplicate experiments. Error bars indicate SD.

(FIG. 5A) Crystal structure of T3D σ3 (011 and et al., 2001), in which cathepsin L cleavage sites are depicted in blue between amino acids 243 and 244 and between 250 and 251 (Ebert et al., 2002). Surrounding residues, from amino acids 241 to 253, are shown in yellow. The C-terminal residues of σ3, from amino acids 340 to 365, are colored red. Tyr354, which is altered in several PI (Wetzel et al., 1997), D-EA (Ebert et al., 2001), and ACA-D viruses (Clark et al., 2006), is shown in green. The virion-distal end of σ3 is at the top of the figure, and the virion-proximal end and N-terminus are at the bottom. The inset shows an enlarged view of the boxed region of σ3 using the same color scheme. Side chains of amino acids 243, 244, 250, 251, and 354 are depicted in ball-and-stick representation. (FIG. 5B) Chymotrypsin treatment of rsT3D and rsT3D-σ3Y354H. Purified virions were treated with chymotrypsin for the indicated intervals and loaded into wells of 10% polyacrylamide gels. After electrophoresis, the gels were stained with Coomassie blue. Viral proteins are labeled on the right. Images were cropped and processed using the auto-contrast feature of Adobe Photoshop. The experiments shown are representative of two performed for each virus. (FIG. 5C) Growth of rsT3D and rsT3D-σ3Y354H in L cells treated with E64. L cells were preincubated in medium with or without E64 at the concentrations shown. The medium was removed, cells were adsorbed with virus for 1 h, and fresh medium with or without E64 was added. After 24 h incubation, viral titers in cell lysates were determined by plaque assay. The results are presented as the mean viral yields, calculated by dividing the titer at 24 h by the titer at 0 h for each concentration of E64, for triplicate experiments. Error bars indicate SD.

FIG. 6A-C. Expression of GFP by rsT3D/S4GFP. (FIG. 6A) Schematic of pT7-S4GFP. The GFP open reading frame is flanked by S4 gene nucleotides 1-149 and 769-1196. (FIG. 6B) Electropherotypes of rsT3D and rsT3D/S4GFP. Viral dsRNA was extracted from purified virions and electrophoresed in an SDS-polyacrylamide gel, followed by ethidium bromide staining to visualize viral gene segments. Size classes of gene segments (L, M, S) are indicated. (FIG. 6C) L cells were infected with rsT3D/S4GFP, stained with antibodies to μNS (blue) and σ3 (red) proteins, and imaged by confocal laser scanning microscopy at the times shown. Scale bar, 10 μM.

FIGS. 7A-B. Experimental strategy to generate reovirus from six plasmids containing cloned cDNAs of reovirus gene segments. (FIG. 7A) Prototype reovirus gene segment cDNA in plasmid. Cloned cDNAs representing each of the 10 full-length reovirus RNA gene segments are flanked by the bacteriophage T7 RNA polymerase promoter (T7P) and the antigenomic hepatitis delta virus (HDV) ribozyme (Rib). (FIG. 7B) Schematic of the approach. A total of six mono-, bi-, and tri-cistronic reovirus cDNA constructs are transfected into L cells expressing T7 RNA polymerase from recombinant vaccinia virus strain rDIs-T7pol, which is replication defective. Nascent transcripts contain the native 5' end whereas autocleavage by the HDV ribozyme generates the natural viral 3' end. Following 2-5 d of incubation, transfected cells are lysed by freeze-thaw, and viable viruses rescued from cloned cDNAs are isolated by plaque assay using L cells.

Figure 1:
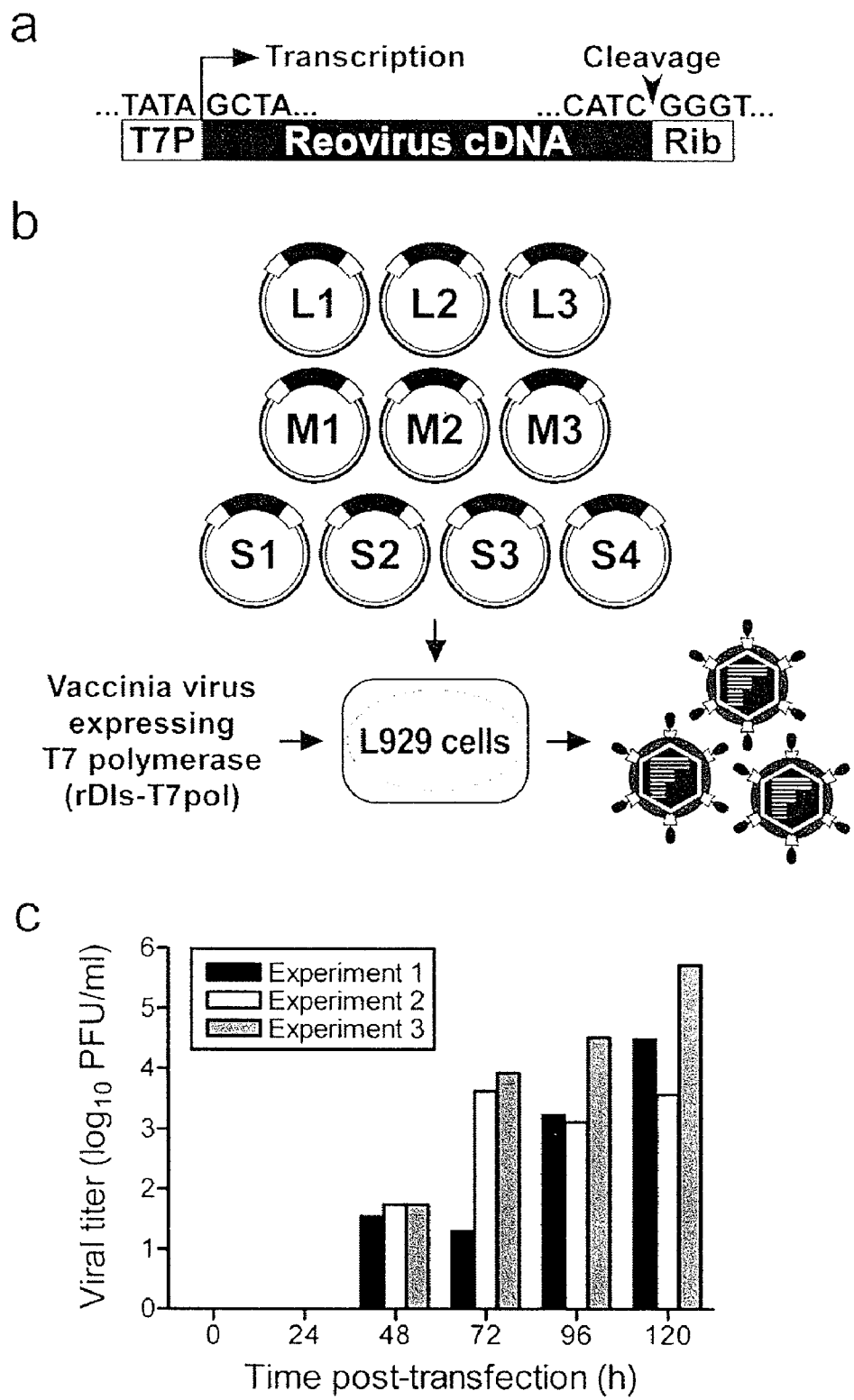
FIGS. 1A-C. Experimental strategy to generate reovirus from cloned cDNA.

DESCRIPTION OF ILLUSTRATIVE
EMBODIMENTS

The absence of DNA intermediates in the life cycle of RNA viruses poses an exceptional technical challenge to genetic analysis of viral phenotypes. Prior to the development of reverse genetics, or "marker rescue," for RNA viruses of animals, in which plasmid-borne cDNAs of viral genomes initiate synthesis of replication-competent RNAs, classic Darwinian methods were used to select viral mutants that could be subjected to correlative genetic studies—so-called "forward genetics." However, reverse genetics technology permits testing of tightly focused, rational hypotheses about complex questions of virus structure, virus-cell interactions, and viral pathogenesis through direct engineering of the viral genome without a need to devise complicated selection strategies for isolation of viral mutants. Furthermore, reverse genetics of RNA viruses has supported rapid exploration of vaccines against these and other infectious agents and propelled their use as gene delivery vehicles (Blaney et al., 2006; Horimoto and Kawaoka, 2006; Riezebos-Brilman et al., 2006).

The inventors now report the development of an entirely plasmid-based reverse genetics system for mammalian reoviruses in which viable viruses are generated from cloned cDNAs. Neither helper virus nor coexpression of viral replication proteins is required for recovery of wild-type (wt) virus or engineered viral mutants. Using this reovirus reverse genetics system, the inventors have revealed new insights into mechanisms of viral cell entry, virus-induced apoptosis, and viral pathogenesis mediated by proteins of the reovirus outer capsid, thus demonstrating the tractability of this technology. The establishment of plasmid-based reverse genetics for reovirus will allow heretofore technically unapproachable problems in dsRNA virus biology to be studied, provide a platform for development of analogous marker rescue systems for other segmented dsRNA viruses, and foster exploration of reoviruses as modalities to elicit protective immunity against a variety of mucosal pathogens.

The system permits selective introduction of desired mutations into cloned cDNAs encoding each of the 10-12 viral gene segments, followed by isolation of mutant viruses from cells transfected with the plasmid constructs. Importantly, recombinant viruses are generated without a requirement for helper virus and free of any selection. Thus, this new technique provides a means to directly and precisely engineer the viral genome in the context of infectious virus. For example, this system was used to engineer mutations in the σ1, σ3, and μ1 proteins. These proteins form part of the viral outer capsid, which is responsible for numerous major events in reovirus interaction with the cell and host, including attachment, disassembly within endosomes, penetration of cell membranes, induction of apoptosis, growth in the intestine and dissemination from that site, pathways of spread, neurovirulence, and tropism within the CNS (for reviews, see Chandran and Nibert, 2003; O'Donnell et al., 2003; Guglielmi et al., 2006).

In addition to its contributions to dsRNA virus research, the reovirus reverse genetics system possesses significant potential as a gene delivery vehicle, principally in three arenas: vaccines, oncolytics, and gene-transfer vectors for research. First, genetically engineered reoviruses are excellent candidates for development of a multifunctional vaccine modality to elicit mucosal immunity. This is a very appealing idea since reovirus undergoes primary replication in intestinal tissue with few or no symptoms in humans (Tai et al., 2005). Secondly, reoviruses generated through reverse-genetics methods may serve as potent oncolytics. Reoviruses have been used for selective lysis of several different tumor cell types in vitro and in experimental animals (Coffey et al., 1998; Hirasawa et al., 2002). Furthermore, wild-type reoviruses have shown efficacy as a virotherapeutic for aggressive and refractory human tumors, such as glioblastoma (Wilcox et al., 2001). Phase II clinical trials to evaluate reovirus as a cancer therapy are ongoing (Stoeckel and Hay, 2006). Reverse genetics will allow generation of a library of highly oncotropic viruses capable of targeting a wide array of tumor types in vivo with minimal risk to normal cells and tissues. Moreover, it may be feasible to engineer reoviruses with genes that are directly tumoricidal or sensitizing to the action of conventional antineoplastic drugs, leading to more potent and specific oncolysis. Finally, reovirus reverse genetics allows dsRNA viruses to be developed as transfection vectors for high-level expression of foreign proteins in animal cells. Expression of reovirus genes is extraordinarily efficient in infected cells, overcoming cellular antiviral responses that result in cessation of host-cell protein synthesis (Smith et al., 2006). Reoviruses also exhibit broad cell and tissue tropism, replicating to high titers in most cell types and thus may provide a useful alternative to currently available virus-based gene-transfer systems.

Ideal reovirus vectors will contain stable σ1 proteins, combine excellent extracellular stability with highly efficient intracellular disassembly, and induce minimal apoptosis. Each of these parameters can be independently adjusted through strategic alterations in outer-capsid proteins. Manipulation of inner-capsid proteins and the genomic RNA itself should allow construction of viruses able to circumvent other aspects of virus-cell and virus-host interactions that pose potential barriers to antigen and gene delivery by reoviruses, e.g., innate and adaptive immune responses.

I. REOVIRIDAE

Beginning in 1959, viruses that were typically isolated from the respiratory and gastrointestinal tracts and not associated with any known disease state were classified as reovirus (respiratory enteric orphan viruses) (Sabin, 1959). During the 1970s, the family enlarged and currently constitutes nine genera. The general characteristics of the Reoviridae family are non-enveloped, 70 to 85 nm in diameter, double protein capsid shell, nearly spherical icosahedron shape, and genome comprised of 10-12 segments of doubled-stranded RNA (dsRNA). Of the 11 genera, four—Orthoreovirus, Rotavirus, Coltivirus, and Seadornavirus—infect humans. These viruses have similar structural features and replicative strategies.

Reoviruses are resistant to solvents, quaternary ammonium salts, phenol, alcohol, pH and heat (50° C. for 1 hr). These viruses survive pasteurization and the most common human strains are also the most common bovine strains. Although reoviruses are not known to be associated with any particular disease, most people have been exposed to these agents by the time they reach early adulthood (Jackson & Muldoon, 1973; Stanley, 1974; Tai, 2005 #4971).

Reoviruses attach to host cells via the filamentous attachment protein, σ1 (Furlong et al., 1988; Fraser et al., 1990). The σ1 protein of all three reovirus serotypes engages junctional adhesion molecule-A (JAM-A) (Barton et al., 2001b; Campbell et al., 2005), an integral component of intercellular tight junctions (Martin-Padura et al., 1998; Liu et al., 2000). Following attachment to cell-surface receptors, reovirus internalization is mediated by β1 integrins (Maginnis et al., 2006), most likely via clathrin-dependent endocytosis (Ehrlich et al., 2004). In the endocytic compartment, reovirus outer-capsid protein σ3 is removed by acid-dependent cysteine proteases in most cell types (Baer and Dermody, 1997; Ebert et al., 2002). Removal of σ3 results in the exposure of a hydrophobic conformer of the viral membrane-penetration protein, μ1, which pierces the endosomal membrane allowing delivery of transcriptionally active reovirus core particles into the cytoplasm (Chandran et al., 2002; Odegard et al., 2004) where the remainder of the replication cycle is completed.

The normal mode of viral transmission for reovirus depends on the virus surviving the environment and passage through the gut to find a few permissive rapidly dividing cells in the intestine. In these cells, the virus replicates to a lytic endpoint. With so few cells involved, symptoms do not result. The viruses are shed into the environment to complete the cycle (Neutra, 1999). It is important to note that the virus has no latent state—if the virus is not blocked intracellularly, replication progresses invariably to cell lysis—the mechanism of viral release.

A. Reovirus

Of particular interest to the present invention is the use of an Orthoreovirus. It is well known to those of skill in the art that the common name for the family Reoviridae and for the specific genus Orthoreovirus is simply reovirus. Thus, in the present invention, the term "reovirus" is all inclusive of the genus Orthoreovirus and all of the viruses contained within this genus, for example, but not limited to mammalian reovirus, avian reovirus, and Nelson Bay virus.

In this genus, the virions measure 60-80 nm in diameter and possess two concentric capsid shells, each of which is icosahedral. The genome consists of double-stranded RNA in 10 discrete segments, with a total genome size of approximately 24 kbp encoding 11-12 translated proteins.

Mammalian reoviruses are ubiquitous agents that infect a variety of mammalian species. Although mammalian reoviruses share a common group antigen, three serotypes were identified by neutralization and hemagglutination-inhibition tests. These serotypes were isolated from humans and are as follows: type 1 (prototype strain Lang), type 2 (prototype strain Jones) and type 3 (prototype strains Dearing and Abney) (Sabin, 1959; Fields, 1996).

B. Other Reoviridae Viruses

It is also contemplated that the species in the genus Rotavirus may be used in the present invention. It is well known that rotaviruses and reoviruses share common structural features. Thus, it is within the scope of the present invention that rotaviruses may also be generated using the techniques described herein.

Yet further, the scope of the present invention is not limited to the genera Orthoreovirus and Rotavirus, the present invention also includes the use of other viruses that are classified as a Reoviridae virus and have similar structural features as reovirus.

C. Reoviridae Infectivity of Cells

For mammalian reoviruses, the cell surface recognition signal is sialic acid (Armstrong et al., 1984; Gentsch & Pacitti, 1985; Paul et al., 1989) and JAM-A. (Barton et al., 2001b; Campbell et al., 2005) Reovirus binds efficiently to a multitude of cell lines and as such can potentially target many different tissues.

As described herein cells which are resistant to reovirus infection became susceptible to reovirus infection when transformed by a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription. It is contemplated that the viral gene translation in resistant cells is correlated with phosphorylation of an approximately 65 kDa cell protein, determined to be double-stranded RNA-activated protein kinase (PKR), that was not sufficiently phosphorylated in transformed cells (See U.S. Pat. Nos. 6,136,307 and 6,110,461 incorporated herein by reference). Thus, it is contemplated that reovirus reproduces by using the host cell's Ras pathway machinery in combination with an associated down regulation of PKR.

II. CULTURING REOVIRUS

Cultured cell lines vary to a great extent in their ability to support reovirus production. In U.S. Pat. No. 6,703,232, a variety of cells were employed and HEK 293 cells proved to be very efficient at producing reovirus. HEK 293, Vero and L929 cells were grown to confluence and infected with the reovirus at a multiplicity of infection (m.o.i.) of 1. The yield of virus was determined at various time post infection. HEK 293 cells, which previously had not been reported to support reovirus growth, produced almost 50 times more reovirus at 24 hours post infection than L929 cells, which are routinely used to culture mammalian reovirus. Vero cells produced even less reovirus at this point, yielding 3000 times less reovirus than the HEK 293 cells.

At 36-48 hours post infection, the virus yield in the HEK 293 cells began to plateau, but the titer was still one order of magnitude higher than the titer produced in L929 cells and two orders of magnitude higher than that of Vero cells. It was not until 96 hours post infection that all three cells lines produced about the same titer of reovirus, at $10^9$ to $10^{10}$ per milliliter. These results indicate that the HEK 293 cell is a very efficient system for the production of reovirus, allowing for shortened production time which will markedly reduce the cost of production.

To further optimize the HEK 293 cell production conditions, reovirus was used to infect the HEK 293 cells at various m.o.i., and the yield was determined. The results suggest that a lower m.o.i. was even more advantageous. Thus, at 48 hours post infection, the cells which were inoculated at a m.o.i. of 0.5 produced more than $10^{10}$ viruses per ml, which was the maximal yield at these culture conditions. After this point, the titer went down by about two fold, and reached the maximal yield again at 96 hours. A similar pattern was observed for the culture with an initial m.o.i. of 0.1. Consequently, the best time to harvest reovirus under these culture conditions appears to be 36-60 hours post infection. At this period of time, the titer is high, and the virus is still associated with the cell fragments and membranes, which makes purification of the virus relatively simple. At 96 hours, all the cells have lysed and the virus is released into the media along with the degradation products of the dead cells, making purification much more complicated than when the virus is cell associated.

For best efficiency, the virus should be harvested when the yield is sufficiently high but most of the virus is still associated with the cells. The harvest time should be determined empirically when culture conditions are varied. To determine if the virus is associated with the cells, a small aliquot of the culture can be examined, e.g., under microscopy, to determine the degree of cell viability at different time points after infection. Alternatively, a vital staining can be conducted to determine the percentage of viable cells. To simplify the purification process, the virus is typically harvested before all the cells have been lysed. Preferably, the virus is harvested when 20-95% of the cells remain viable. More preferably, the virus is harvested when 35-90%, and most preferably 50-80%, of the cells remain viable.

HEK 293 cells are adherent cells and can be grown in cell culture flasks, roller bottles, microcarrier systems or hollow fiber systems, or any other system that is suitable for growing adherent cells. HEK 293 cells may be modified to generate derivative cells. For example, the 293/SF cell (ATCC Number CRL-1573.1) was derived from the HEK 293 cell and adapted to serum-free culture conditions. The 293/SF cells grow as a mixture of adherent and suspension cells and may be grown in any of the culture containers described above, as well as spinner bottles, stirred vessels (fermenters), hollow fiber systems, or any other culture containers suitable for suspension cells.

In order to produce industrial amounts of reovirus, 293/SF cells can be cultured in 15 L spinner flasks and infected with reovirus at a multiplicity of infection of 0.5 when cell density reaches $10^6$ cells/ml. The culture is incubated until cell lysis begins, as evidenced by the culture media color change from red to orange due to the presence of Phenol Red in the media, or by a viable cell count under the microscope. At this point, the virus may be harvested by centrifugation. The virus can then purified as described below. For storage, the virus can be frozen or lyophilized according to methods established in the art, with or without stabilizing agents.

III. PURIFICATION OF VIRUS

It may be desirable to purify the Reoviridae virus, modified virus or variants thereof. Purification techniques are well known to those of skill in the art. Analytical methods particularly suited to the preparation of a pure viral batch are tangential flow concentration or cesium chloride ultra-centrifugation (January, 1971).

Certain aspects of the present invention concern the purification, and in particular embodiments, the substantial purification, of the modified virus. The term "purified modified virus" as used herein, is intended to refer to a virus or viral batch or viral stock that is purified to any degree relative to its naturally-obtainable state.

Generally, "purified" will refer to a virus or viral batch or stock that has been subjected to fractionation to remove various other components, such as unreactive PEG, and which composition substantially retains its expressed biological activity. Where the term "substantially purified" is used, this designation will refer to a composition in which the virus or viral batch or viral stock forms the major component of the composition, such as constituting about 70%, 80%, 90%, 95% or 99% or more of the virus or viral batch or viral stock in the composition.

Yet further, the virus can be purified by affinity purification with elution at low pH. The virus is then concentrated by saturated ammonium sulfate and dialyzed by tangential flow to remove small molecules.

Various methods for quantifying the degree of purification of the virus or viral batch or viral stock will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the virus or viral batch or viral stock exhibits a detectable activity. In specific embodiments, the tissue infective dose (TID) per unit protein of the crude cell lysate is calculated and compared to the TID/protein ratio of the purified viral fraction and to the TID/protein ratio following cesium chloride gradient purification.

IV. VECTORS

The term Reoviridae "vector" is used herein to refer to a nucleic acid molecule or molecules that is capable of encoding all of the elements necessary to generate a viable or infectious genome that can replicate. The vector may also contain other nucleic acid sequences, i.e., non-viral sequences, that may encode non-viral products or support the transcription or translation of any vector-encoded (viral or non-viral) material. Vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. One of skill in the art would be able to identify and incorporate a wide variety of these sequences into the vectors of the present invention through standard recombinant techniques (see, for example, Maniatis et al., 1988, and Ausubel et al., 1994, both incorporated herein by reference).

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally-associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 2001, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a phage T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), and human platelet endothelial cell adhesion molecule-1 (Almendro et al., 1996).

Examples of promoters which are operative in insect cells include polyhedrin promoter, P10 promoter, basic protein promoter of Autographa californica nuclear polyhedrosis, baculovirus immediate early gene 1 promoter, baculovirus 39K delayed early gene promoter, and the like. Examples of promoters which are operative in yeast host cells include a promoter derived from yeast glycolysis system genes, alcohol dehydrogenase gene promoter, TPI1 promoter, ADH2-4c promoter, and the like.

B. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

C. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999; Levenson et al., 1998; and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

E. Termination Signals

The vectors or constructs of the present invention will generally comprise at least one termination signal. A "termination signal" or "terminator" is comprised of the DNA sequences involved in specific termination of an RNA transcript by an RNA polymerase.

Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

F. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

G. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

H. Selectable Markers

In certain embodiments of the invention, cells containing a nucleic acid construct of the present invention may be identified in vitro or in vivo by including a marker in the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. Further examples of selectable markers are well known to one of skill in the art.

V. MODIFICATIONS TO REOVIRAL GENOMES

A. Mutations in Reoviral Genes

In principle, any mutation, in the form of point substitution, insertion, or deletion, that is compatible with viral viability may be recovered in the genomes of infectious virion particles using the present invention. These include alterations in outer-capsid proteins (e.g., Γ1, σ3, and μ1 of mammalian reovirus) to reprogram viral receptor specificity, augment extracellular particle stability, enhance intracellular particle disassembly and transcriptional activation, regulate apoptosis, and modify particle antigenicity. Mutations of proteins comprising the inner shell (e.g., λ1, λ2, λ3, μ2, and σ2 of mammalian reovirus), including the viral RNA-dependent RNA polymerase, also are envisioned for regulation of replication and transcriptional efficiency as well as packaging of nonviral and modified viral RNAs. Alterations of viral nonstructural (replication) proteins (e.g., μNS, σNS, and σ1s of mammalian reovirus) are considered for the modulation of viral yields from infected cultures and adaptation of viral growth to various environmental conditions (e.g., increased or decreased temperature). Finally, for the purpose of maximizing incorporation efficiency of nonviral RNAs into infectious virion particles, mutations in viral RNAs are contemplated that do not introduce changes in the encoded protein products, but rather alter RNA-RNA interactions that impose restraints on RNA packaging specificity and capacity.

Non-Reoviridae Proteins for Viral Expression

A variety of foreign (heterologous) proteins may be included in the engineered Reoviridae vectors of the present invention. For example, genes encoding enzymes, hormones, cytokines, oncogenes, receptors, tumor suppressors, transcription factors, drug selectable markers, fluorescent or luminescent marker proteins, toxins and various antigens are contemplated as suitable genes for use according to the present invention. In addition, antisense, ribozyme and intefering RNAs can be expressed from vectors of the present invention.

1. Anti-Cancer Genes p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and EIB. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^{B}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo.

Other tumor suppressors that may be employed according to the present invention include RB, APC, DCC, NF-1, NF-2, WT-1, MEN-I, MEN-II, zac1, p73, VHL, MMAC1, FCC, FHIT, FUS-1, MDA7 and MCC. Inducers of apoptosis, such as Bax, Bak, Bc1-$X_s$, Bik, Bid, Harakiri, Ad E1B, Bad and ICE-CED3 proteases, similarly could find use according to the present invention.

2. Enzymes

Various enzyme genes may be expressed according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

3. Hormones

Hormones are another group of gene that may be used in the SV40 vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

4. Cytokines/Interleukins/Inteferons

Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, GM-CSF, G-CSF, interferon α, interferon β and interferon γ.

5. Antigens

Other therapeutics genes might include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, retrovirus, papovavirus, parvovirus, herpesvirus, poxvirus, hepadnavirus, and spongiform virus. Particular viral targets include influenza, herpes simplex virus 1 and 2, measles, smallpox, polio or HIV. Preferred examples include HIV env and gag proteins and hepatitis B surface antigen. Parasitic pathogens include protozoa, trypanosomes, tapeworms, roundworms, and helminths. Also, tumor markers, such as fetal antigen or prostate specific antigen, may be targeted in this manner.

6. Antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody. Antibodies to a wide variety of molecules are contemplated, such as oncogenes, toxins, hormones, enzymes, viral or bacterial antigens, transcription factors or receptors.

7. Inhibitory Nucleic Acid Sequences

Another class of molecules that could be expressed in target cells is antisense molecules. Antisense methodology takes advantage of the fact that nucleic acids tend to pair with "complementary" sequences, thereby inhibiting transcription and/or translation of the corresponding gene and gene product, respectively. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. Antisense constructs may be designed to bind to the promoter and other control regions, exons, introns or even exon-intron boundaries of a gene. Suitable targets for antisense therapies include pathogen genes as well as oncogenes, including ras, myc, neu, raf, erb, src, fms, jun, trk, ret, gsp, hst, bcl and abl.

RNA interference ($RNA_i$) is a form of gene silencing triggered by double-stranded RNA (dsRNA). dsRNA activates post-transcriptional gene expression surveillance mechanisms that appear to function to defend cells from virus infection and transposon activity. Fire et al. (1998); Grishok et al. (2000); Ketting et al. (1999); Lin & Avery (1999); Montgomery et al. (1998); Sharp (1999); Sharp & Zamore (2000); Tabara et al. (1999). Activation of these mechanisms targets mature, dsRNA-complementary mRNA for destruction. RNA, offers major experimental advantages for study of gene function. These advantages include a very high specificity, ease of movement across cell membranes, and prolonged down-regulation of the targeted gene. Fire et al. (1998); Grishok et al. (2000); Ketting et al. (1999); Lin & Avery (1999); Montgomery et al. (1998); Sharp (1999); Sharp & Zamore (2000); Tabara et al. (1999). Moreover, dsRNA has been shown to silence genes in a wide range of systems, including plants, protozoans, fungi, *C. elegans, Trypanasoma* and *Drosophila.* Grishok et al. (2000); Sharp (1999); Sharp & Zamore (2000).

Interestingly, $RNA_i$ can be passed to progeny, both through injection into the gonad or by introduction into other parts of the body (including ingestion) followed by migration to the gonad. Several principles are worth note (see Plasterk & Ketting, 2000) First, the dsRNA should be directed to an exon, although some exceptions to this rule have been shown. Second, a homology threshold (probably about 80-85% over 200 bases) is required. Most tested sequences are 500 base pairs or greater. Third, the targeted mRNA is lost after $RNA_i$. Fourth, the effect is non-stoichometric, and thus incredibly potent. In fact, it has been estimated that only a few copies of dsRNA are required to knock down>95% of targeted gene expression in a cell. Fire et al. (1998).

Although the precise mechanism of RNA; is still unknown, the involvement of permanent gene modification or the disruption of transcription have been experimentally eliminated. It is now generally accepted that RNA, acts post-transcriptionally, targeting RNA transcripts for degradation. It appears that both nuclear and cytoplasmic RNA can be targeted. Bosher and Labouesse (2000).

8. Marker Proteins

The present invention also contemplates expression of proteins that are detectable or selectable. Various detectable markers include the fluorescent and chemiluminescent proteins such as luciferase, GFP, CFP, YFP, as well as variants thereof. Also contemplated are selectable markers such as antibiotic resistance markers (chloramphenicol, ampicillin, HGPRT, etc.).

VI. NUCLEIC ACID DELIVERY AND CELL TRANSFORMATION

In certain embodiment, the present invention will employ gene transfer techniques to build the recombinant reoviruses of the present invention. Suitable methods for delivery to cells of a reovirus genome or fragments thereof into a cell are known to one of ordinary skill in the art. Such methods include, but are not limited to, direct delivery of DNA such as by ex vivo transfection (Wilson et al., 1989; Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome-mediated transfection/lipofection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610, 042; 5,322,783 5,563,055, 5,550,318, 5,538,877 and 5,538, 880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952, 500, each incorporated herein by reference); by desiccation/ inhibition-mediated DNA uptake (Potrykus et al., 1985); and any combination of such methods. Through the application of techniques such as these, organelle(s), cell(s), tissue(s) or organism(s) may be stably or transiently transformed.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cells and viruses. L cells and HeLa cells were maintained as described (Barton et al., 2001a). Reovirus strains T1L and T3D are laboratory stocks originally obtained from Dr. Bernard Fields. Virus was purified after growth in L cells by CsCl-gradient centrifugation (Furlong et al., 1988). Purified $^{35}$S-methionine-labeled virions were prepared as described (Nibert et al., 1995). Attenuated vaccinia virus strain rDIs-T7pol expressing T7 RNA polymerase was propagated in chick embryo fibroblasts as described (Ishii et al., 2002).

Plasmid construction. Full-length reovirus cDNAs were amplified by RT-PCR using viral dsRNA extracted from purified virions as template. Amplified cDNAs were initially cloned into pBluescript II SK (−) (Stratagene) for the T3D L1, L2, and L3 genes or pCR 2.1 (Invitrogen) for the T3D M1, M2, M3, S1, S2, S3, and S4 genes and the T1L S1 gene. To generate pT7-L1T3D, pT7-L2T3D, pT7-L3T3D, pT7-M1T3D, pT7-M2T3D, pT7-M3T3D, pT7-S2T3D, pT7-S3T3D, and pT7-S4T3D, viral cDNA-containing fragments were subcloned into p3E5EGFP (Watanabe et al., 2004). Viral cDNAs fused at their native 5' termini to the phage T7 RNA polymerase promoter were inserted into p3E5EGFP by partial or complete replacement of plasmid sequences encoding GFP and the Ebola virus leader and trailer, resulting in ligation of native 3' termini to the HDV ribozyme sequence. To generate pBacT7-S1 T3D and pBacT7-S1T1L, encoding the T3D S1 and T1L S1 genes, respectively, S1 cDNAs fused to the T7 promoter and a portion of the HDV ribozyme were first cloned into the BseRI site of p3E5EGFP, and fragments containing the S1 gene flanked 5' by the T7 promoter and 3' by the HDV ribozyme and T7 terminator sequences were subcloned into the Xba1 site of pBacPAK8 (Clontech). pBacT7-S1T3D and pT7-S4T3D were used as templates to generate mutant constructs pBacT7-S1T3DT249I and pT7-S4T3DY354H, respectively, by introduction of specific nucleotide substitutions using the QuickChange site-directed mutagenesis kit (Stratagene) (Supplemental Table 3). To generate pT7-S4GFP, S4 nucleotide sequences 150-768 within pT7-S4T3D were replaced with the GFP open reading frame (ORF). Nucleotide sequences of recombinant plasmids were confirmed by DNA sequencing.

Plasmid transfection and recovery of recombinant virus. Monolayers of L cells at approximately 90% confluence ($3 \times 10^6$ cells) in 60 mm dishes (Costar) were infected with rDIs-T7pol at an MOI of ~0.5 TCID50. At 1 h post-infection, cells were cotransfected with ten plasmid constructs representing the cloned T3D genome—pT7-L1T3D (2 µg), pT7-L2T3D (2 µg), pT7-L3T3D (2 µg), pT7-M1T3D (1.75 µg), pT7-M2T3D (1.75 µg), pT7-M3T3D (1.75 µg), pBacT7-S1T3D (2 µg), pT7-S2T3D (1.5 µg), pT7-S3T3D (1.5 µg), and pT7-S4T3D (1.5 µg)—using 3 µl of TransIT-LT1 transfection reagent (Mirus) per µg of plasmid DNA. Following 0 to 5 days of incubation, recombinant virus was isolated from transfected cells by plaque purification on monolayers of L cells (Virgin et al., 1988). Electrophoretic analysis of viral dsRNA was performed as described (Wilson et al., 1996). Confirmation of mutations in the S1, S4, and L1 genes of recombinant viruses was performed using the Onestep RT-PCR kit (Qiagen), gene-specific primer sets, and viral dsRNA extracted from purified virions as template. Purified PCR products were subjected directly to sequence analysis.

Immunofluorescence of reovirus infection. Regular L cells ($5\times10^4$) or transfectants selected for stable expression of σ3 protein ($5\times10^4$) were plated on glass coverslips in 24-well plates (Costar) and infected at an MOI of 10,000 (T3D and rsT3D) or 20,000 (rsT3D/S4-GFP) particles/cell. Following 18 h or 24 h incubation at 37° C., cells were fixed and stained for µNS and σ3 proteins as described (Maginnis et al., 2006). Images were captured on a Zeiss LSM 510 Meta confocal microscope (Carl Zeiss) and processed using LSM 510 Meta software (Carl Zeiss) and MetaMorph image analysis software (Molecular Devices).

Infectivity of recombinant viruses. Monolayers of L cells ($2.5\times10^5$) in 24-well plates or suspension cultures of MEL cells ($5\times10^5$ cells/ml) were infected with virus at an MOI of 2 PFU/cell. After 1 h adsorption at room temperature, the inoculum was removed, cells were washed twice with PBS, and fresh medium was added. Cells were incubated at 37° C. for various intervals, and viral titers in cell lysates were determined by plaque assay (Virgin et al., 1988).

Analysis of viral capsid proteins following protease treatment. Purified virions at a concentration of either $2\times10^{12}$ particles/ml (trypsin) or $9\times10^{12}$ particles/ml (chymotrypsin) were digested with either 50 µg/ml of N α-p-tosyl-L-sulfonyl phenylalanyl chloromethyl ketone-treated bovine trypsin (Sigma) or 200 µg/ml of Nα-p-tosyl-L-lysine chloromethyl ketone-treated bovine α-chymotrypsin (Sigma) for various intervals at either 25° C. (trypsin) or 8° C. (chymotrypsin) as described (Nibert et al., 1995; Wetzel et al., 1997). Protease digestion was stopped by adding either 0.5 mg/ml soybean trypsin inhibitor (trypsin) (Sigma) or 5 mM phenylmethylsulfonyl fluoride (chymotrypsin) (Sigma) to the treatment mixtures and cooling at 0° C. Viral proteins were resolved by SDS-PAGE and visualized by either autoradiography (Nibert et al., 1995) or staining with Coomassie blue (Wetzel et al., 1997).

Infection of mice. Newborn C57/BL6 mice weighing 2.0-2.5 grams (2 to 4 days old) were inoculated perorally or intracranially with $10^3$ or $10^2$ PFU, respectively, of purified reovirus virions diluted in PBS. PO inoculations (50 µl) were delivered intragastrically as described (Rubin and Fields, 1980). IC inoculations (5 µl) were delivered to the left cerebral hemisphere using a Hamilton syringe and 30-gauge needle (Tyler et al., 1985). At various intervals following inoculation, mice were euthanized, and organs were harvested into 1 ml of PBS and homogenized by freezing, thawing, and sonication. Viral titers in organ homogenates were determined by plaque assay (Virgin et al., 1988). Animal husbandry and experimental procedures were performed in accordance with Public Health Service policy and approved by the Vanderbilt University School of Medicine Institutional Animal Care and Use Committee.

Growth of virus in cells treated with E64. Monolayers of L cells ($2\times10^5$) in 24-well plates were preincubated in medium supplemented with 0 to 200 µM E64 (Sigma) for 4 h. The medium was removed, and cells were adsorbed with virus at an MOI of 2 PFU/cell. After incubation at 4° C. for 1 h, the inoculum was removed, cells were washed with PBS, and 1 ml of fresh medium supplemented with 0 to 200 µM E64 was added. Cells were incubated at 37° C. for 24 h and frozen and thawed twice. Viral titers in cell lysates were determined by plaque assay (Virgin et al., 1988).

Generation of σ3-expressing cells. L cells stably expressing σ3 protein were selected by transfection of cells with pCXN-S4T3D, which encodes the entire T3D σ3 ORF, and incubation in the presence of 1 mg/ml of geneticin (Invitrogen).

Plasmid construction. To construct T3D L1, L3, and M1 plasmid cDNAs for rescue of recombinant infectious reovirus, RT-PCR products generated using viral genomic RNA and gene-specific primer sets (Supplemental Table 3) were cloned into the EcoRV-RsrII (L1 and M1) or SmaI-RsrII site (L3) of p3E5EGFP, resulting in pT7-L1T3D, pT7-L3T3D, and pT7-M1T3D. The T3D L2 gene cDNA, amplified from viral genomic RNA with specific primers, was inserted into the EcoRI-RsrII site of pT7-L3T3D, thereby replacing the L3 cDNA and generating pT7-L2T3D. pT7-M2T3D, containing the T3D M2 gene cDNA, was constructed by RT-PCR amplification of the M2 gene using viral genomic RNA and specific primers and insertion of the resultant cDNA into the EcoRV-BseRI site of p3E5EGFP. To construct pT7-M3T3D, pT7-S2T3D, and pT7-S4T3D, which contain the T3D M3, S2, and S4 genes, respectively, RT-PCR amplification products generated using viral genomic RNA and specific primers were inserted into RsrII (M3) and BseRI (S2 and S4) sites of p3E5EGFP. p3E5EGFP constructs containing cloned T3D M3, S2, and S4 genes were treated with the SmaI and AvrII (pT7-M3T3D) or EcoRV and AvrII (pT7-S2T3D and pT7-S4T3D) and self-ligated to remove GFP-encoding sequences and the Ebola virus leader and trailer. The T3D S3 cDNA was amplified by RT-PCR using viral genomic RNA and gene-specific primer sets and inserted into pCR2.1. The pCR2.1-based construct then was used as template for secondary PCR amplification of S3 sequences with the M13-reverse and gene-specific primers, and the amplification product was inserted into the EcoRV-RsrII site of p3E5EGFP to generate pT7-S3T3D. The T1L and T3D S1 cDNAs were amplified by RT-PCR using viral genomic RNA and gene-specific primer sets containing BseRI sites and inserted into pCR2.1. A BseRI fragment containing the S1 cDNA and T7 promoter was subcloned into p3E5EGFP to generate S1-p3E5EGFP. An XbaI fragment of S1-p3E5EGFP containing the S1 cDNA fused to the T7 promoter and HDV ribozyme was inserted into the XbaI site of pBacPak8 (Clontech) to generate pBacT7-S1T1L or pBacT7-S1T3D. To generate pT7-S4GFP, sequences corresponding to the open reading frame (ORF) of enhanced GFP (pEGFP-N1, Clontech) were substituted for S4 gene nucleotide sequences 150-768 in pT7-S4T3D. A unique EcoRI site first was introduced into the S4 gene of pT7-S4T3D using the QuickChange site-directed mutagenesis kit, yielding the construct, pT7-S4T3DEcoRI. Subsequently, a PCR product containing the GFP ORF was cloned into the EcoRI-XhoI site of pT7-S4T3DEcoRI to generate pT7-S4GFP. The construct, pCXN-S4T3D, which contains the entire T3D σ3 ORF, was created by subcloning T3D S4 sequences from pCMVS4 wt (Becker et al., 2003) into the EcoRI-KpnI site of pCXNMCS, which was derived by modifying the multiple-cloning site of pCXN2 (Niwa et al., 1991).

Example 2

Results

Generation of viable reovirus from cloned cDNA. To generate recombinant reovirus from cloned cDNAs, plasmids encoding each of the 10 viral gene segments were engineered to facilitate transcription of full-length viral mRNAs under control of the bacteriophage T7 RNA polymerase promoter, which directs synthesis of transcripts with native 5' termini (FIG. 1A). Murine L cells, which efficiently support reovirus growth (Barton et al., 2001a), were infected with an attenuated, T7 RNA polymerase-expressing vaccinia virus strain (rDIs-T7pol) 1 h prior to transfection with the 10 reovirus cDNA plasmids (FIG. 1B). Nascent transcripts were synthesized with the hepatitis delta virus (HDV) ribozyme fused to the 3' terminus, which generates a native 3' end upon autocatalytic removal (FIG. 1A). Thus, this expression strategy generates 10 unique reovirus mRNA species competent to complete all steps in the viral RNA life cycle. Accordingly, rescued viruses were recovered from cell-culture supernatants by plaque assay on L-cell monolayers (FIG. 1C).

Figure 2:
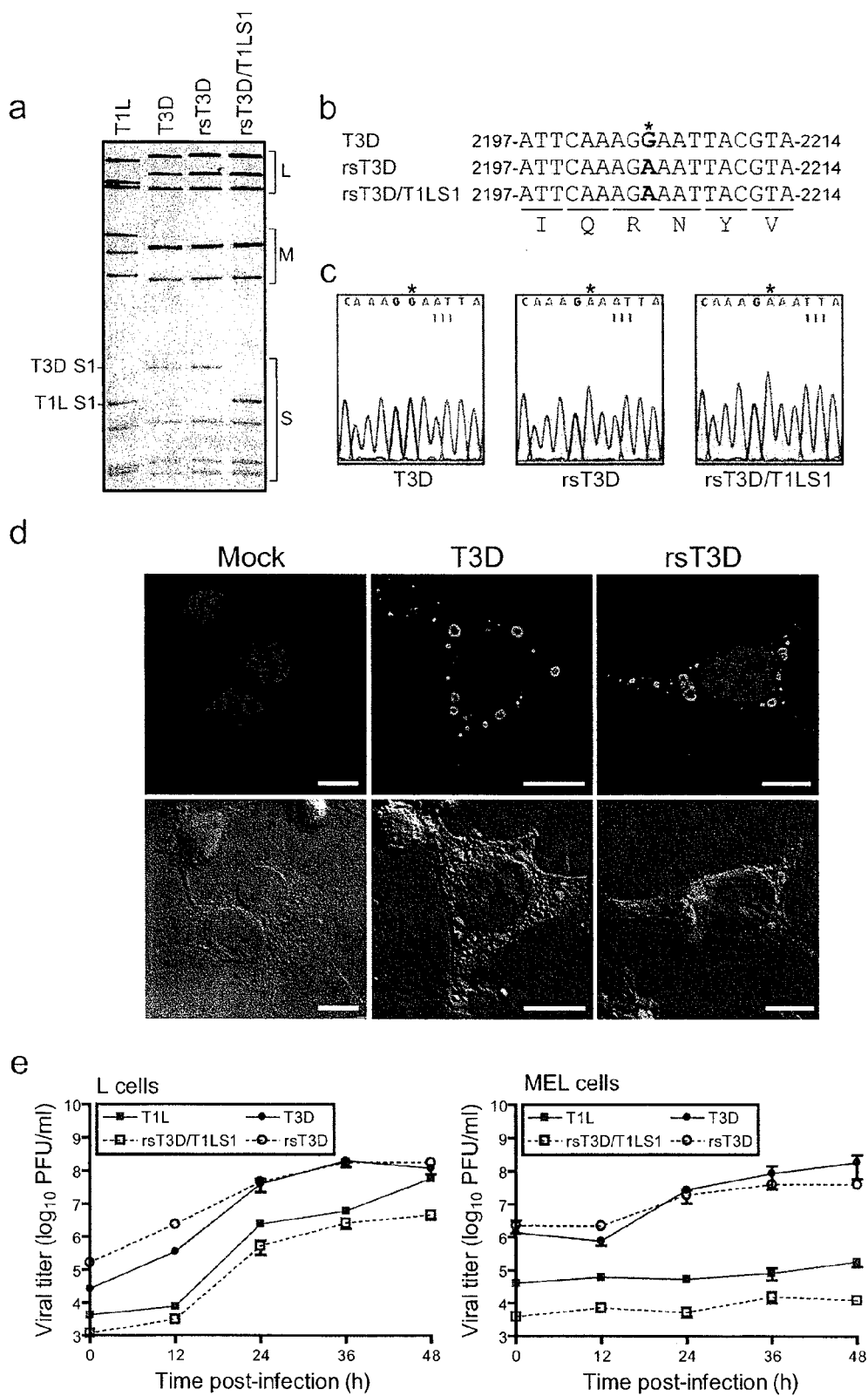
FIGS. 2A-E. Rescue of rsT3D and rsT3D/T1LS1.

Separation of reovirus genomic dsRNA using SDS-PAGE produces unique electrophoretic patterns that can be used to discriminate different viral strains (Barton et al., 2001a). To confirm that viruses isolated using the plasmid-based rescue procedure contained the expected combination of gene segments, genomic dsRNA isolated from recombinant strain (rs) T3D and rsT3D/T1LS1 was resolved in SDS-polyacrylamide gels and visualized by ethidium bromide staining (FIG. 2A). The electropherotype of rsT3D was indistinguishable from that of strain T3D, the origin of the cloned cDNA sequences used to generate rsT3D. Likewise, rsT3D/T1LS1 displayed an electropherotype consistent with its provenance, nine cloned gene segments derived from T3D and a single cloned gene segment, S1, derived from strain T1L. To exclude the possibility of contamination, a silent point mutation, G to A at nucleotide 2205, was introduced into the L1 gene of all virus strains generated from cloned cDNAs (FIG. 2B). This change has not been observed in any reported T3D L1 sequence (Wiener and Joklik, 1989) and serves as a signature for viruses derived through plasmid-based rescue. As anticipated, sequence analysis of rsT3D and rsT3D/T1 LS1 revealed the expected G to A substitution (FIG. 2C), confirming the plasmid origins of these isolates.

Characterization of reoviruses generated by plasmid transfection. Reoviruses replicate and assemble in cytoplasmic inclusions in infected cells known as "viral factories" (Fields, 1971). Viral inclusions contain dsRNA (Silverstein and Schur, 1970), viral proteins (Fields, 1971), and both complete and incomplete particles (Fields, 1971). Reovirus strain T3D forms large globular inclusions that localize to the perinuclear space (Parker et al., 2002). To determine whether rsT3D forms viral inclusions in a manner similar to native T3D, cells were infected with T3D and rsT3D and processed 18 h post-infection for image analysis by confocal microscopy (FIG. 2D). Both T3D and rsT3D formed morphologically indistinguishable large globular inclusions that were localized to the perinuclear compartment. The inventors conclude that recombinant rsT3D recapitulates a hallmark of native T3D infection in cultured cells.

To confirm that the recombinant viruses exhibit growth kinetics similar to the native strains, T1L, T3D, rsT3D, and rsT3D/T1LS1 were tested for the capacity to infect L cells and MEL cells (FIG. 2E). L cells support growth of all reovirus strains tested in our laboratory. In contrast, MEL cells support growth of only sialic acid-binding reovirus strains (Rubin et al., 1992; Chappell et al., 1997). T1L, rsT3D/T1LS1, T3D, and rsT3D produced ~1000-fold yields of viral progeny in L cells. However, only sialic acid-binding strains T3D and rsT3D were capable of efficiently infecting MEL cells, producing yields in each case of ~100-fold, whereas strains T1L and rsT3D/T1LS1 produced minimal yields of viral progeny in these cells (<10-fold). Together, these data indicate that recombinant reoviruses display replication characteristics indistinguishable from native strains.

Figure 3:
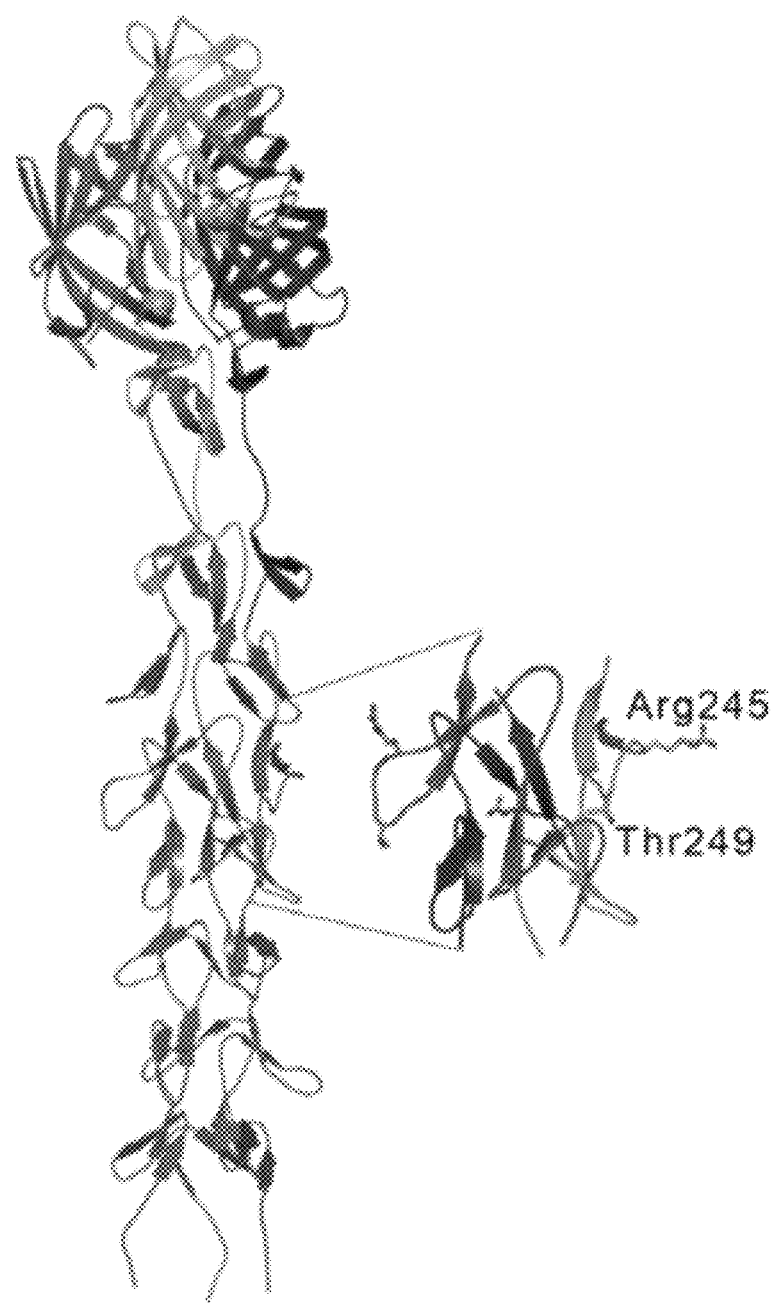
FIGS. 3A-C. The σ1 protein of rsT3D-σ1T249I is resistant to trypsin.
Figure 3:
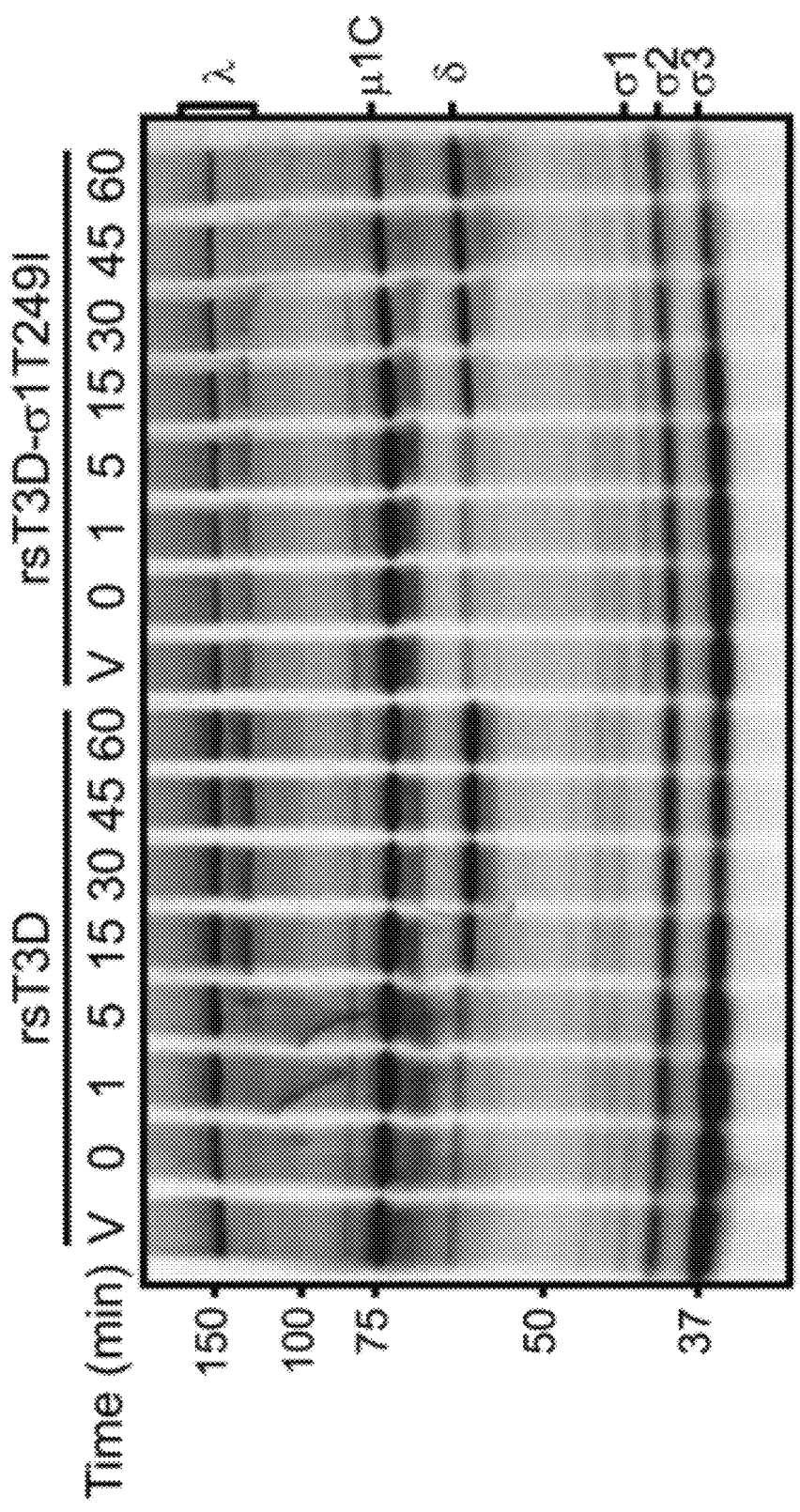
Figure 3:
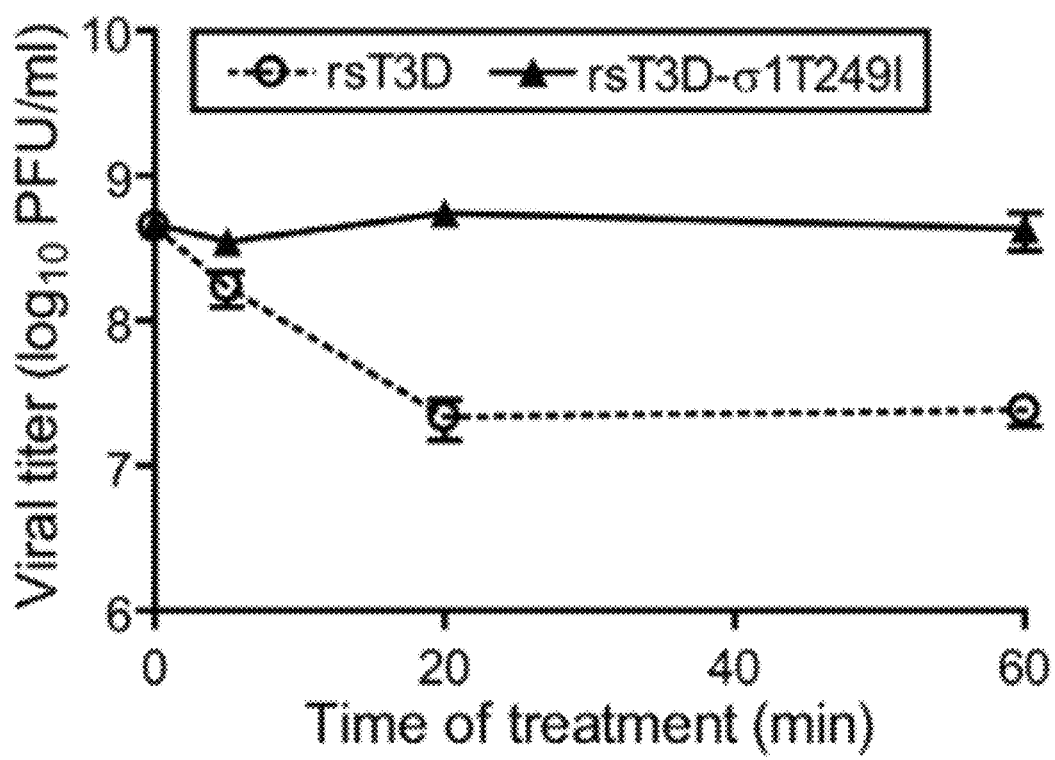

Susceptibility of attachment protein σ1 to proteolytic cleavage attenuates reovirus virulence. The σ1 protein exhibits strain-specific differences in susceptibility to cleavage following in vitro treatment with intestinal proteases to generate ISVPs (Nibert et al., 1995; Chappell et al., 1998). This difference in cleavage susceptibility segregates with a single amino acid polymorphism in the tail domain of σ1 (FIG. 3A). Strains with a threonine at residue 249 in σ1 are susceptible to cleavage by trypsin after Arg245, whereas those with an isoleucine at residue 249 are resistant to cleavage (Chappell et al., 1998). The importance of sequence polymorphism at residue 249 has been confirmed in studies using expressed protein (Chappell et al., 1998) and recoated core particles (Chandran et al., 2001), but not with intact virions.

To determine whether the single Thr-Ile polymorphism at residue 249 in al protein is sufficient to alter σ1 cleavage susceptibility during treatment of virions with intestinal proteases to generate ISVPs, the inventors used plasmid-based rescue to generate rsT3D-σ1T249I, which differs from rsT3D by the presence of an isoleucine in al at residue 249 (Supplemental Table 2). Purified virions of rsT3D and rsT3D-σ1T249I were treated with trypsin and analyzed by SDS-PAGE. As expected, a digestion pattern consistent with formation of ISVPs (loss of σ3 protein and generation of the δ fragment of W C protein) was observed for both viruses (FIG. 3B). However, the stability of rsT3D and rsT3D-σ1T249I σ1 proteins differed. The band corresponding to rsT3D σ1 diminished in intensity immediately after trypsin addition until it was eventually undetectable (FIG. 3B). However, the rsT3D-σ1T249I σ1 band was intact even after 60 min of digestion. Thus, the T249I polymorphism is an independent determinant of σ1 cleavage susceptibility.

Proteolytic cleavage of σ1 at a site adjacent to Thr249 releases the JAM-A-binding σ1 head domain, leading to diminished viral infectivity (Nibert et al., 1995). To test whether rsT3D and rsT3D-σ1T249I differ in infectivity after protease treatment to generate ISVPs, purified virions of each strain were exposed to trypsin for various intervals, and titers of infectious virus in the treatment mixtures were determined by plaque assay (FIG. 3C). As observed with wt T3D in previous experiments (Nibert et al., 1995), rsT3D lost infectious titer rapidly after protease treatment. In contrast, titers of rsT3D-σ1T249I remained relatively stable throughout the assay time course. Loss of infectivity of rsT3D correlated with kinetics of σ1 cleavage (compare FIGS. 3B and 3C), indicating that changes in viral infectivity after trypsin treatment are governed by the cleavage state of σ1. Furthermore, both phenotypes are linked to a single σ1 polymorphism at amino acid 249.

Figure 4:
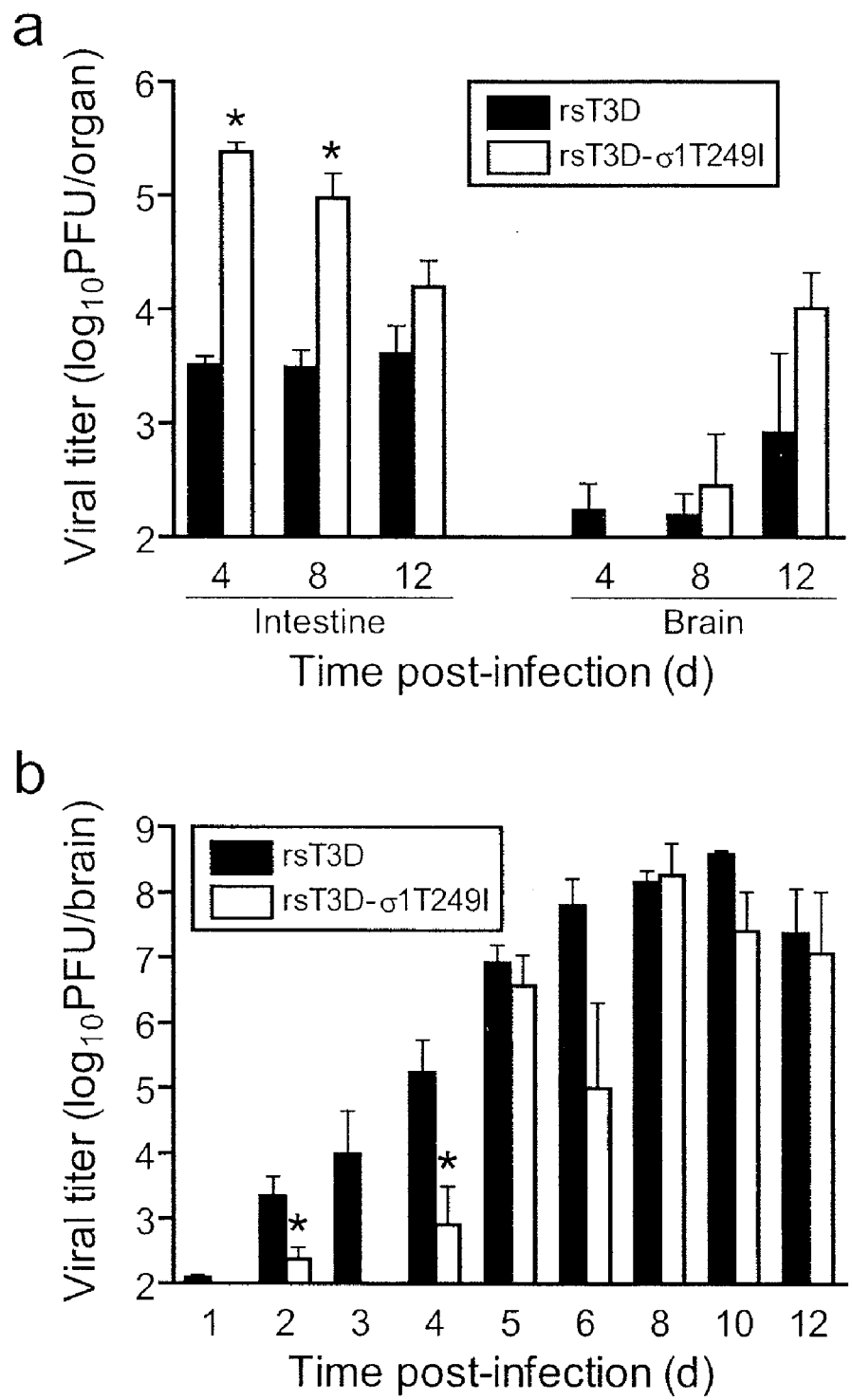
FIGS. 4A-B. rsT3D-σ1T249I infects the murine intestine and disseminates to the CNS. Titers of rsT3D and rsT3D-σ1T249I after either (FIG. 4A) PO or (FIG. 4B) IC inoculation. Mice were inoculated with virus and euthanized at the indicated times post-inoculation. Viral titers in organ homogenates were determined by plaque assay. Each data point represents the average viral titer from 3-6 mice. Error bars indicate SD. *, $P<0.05$ by Student's t test in comparison to rsT3D.

Reovirus strains T1L and T3D differ in the capacity to infect the murine intestine after peroral (PO) inoculation (Bodkin et al., 1989), a property that segregates with the viral S1 (encoding σ1 and σ1s) and L2 (encoding λ2) genes (Bodkin and Fields, 1989). Exposure of T3D to an intestinal wash results in σ1 cleavage (Chappell et al., 1998), raising the possibility that failure of T3D to infect the intestine is in part attributable to σl cleavage susceptibility. To test whether susceptibility of σ1 to proteolytic cleavage is associated with diminished T3D virulence in animals, the inventors assessed the capacity of rsT3D and rsT3D-σ1T249I to infect the intestine and disseminate systemically following PO inoculation (FIG. 4A). Newborn mice were inoculated perorally with each strain, and viral titers in the intestine and brain were determined at 4, 8, and 12 days after inoculation. At all time points tested, titers of rsT3D-σ1T249I in the intestine were greater than those produced by rsT3D. Furthermore, rsT3D-σ1T249I produced greater titers in the brain at days 8 and 12 than did rsT3D. However, when inoculated by the intracranial (IC) route, rsT3D and rsT3D-σ1 T249I produced equivalent titers (FIG. 4B), although rsT3D reached peak titers at earlier time points than did rsT3D-σ1T249I. These findings indicate that a Thr-Ile polymorphism at amino acid 249 in T3D-σ1 controls viral growth in the murine intestine and systemic spread to the CNS.

Figure 5:
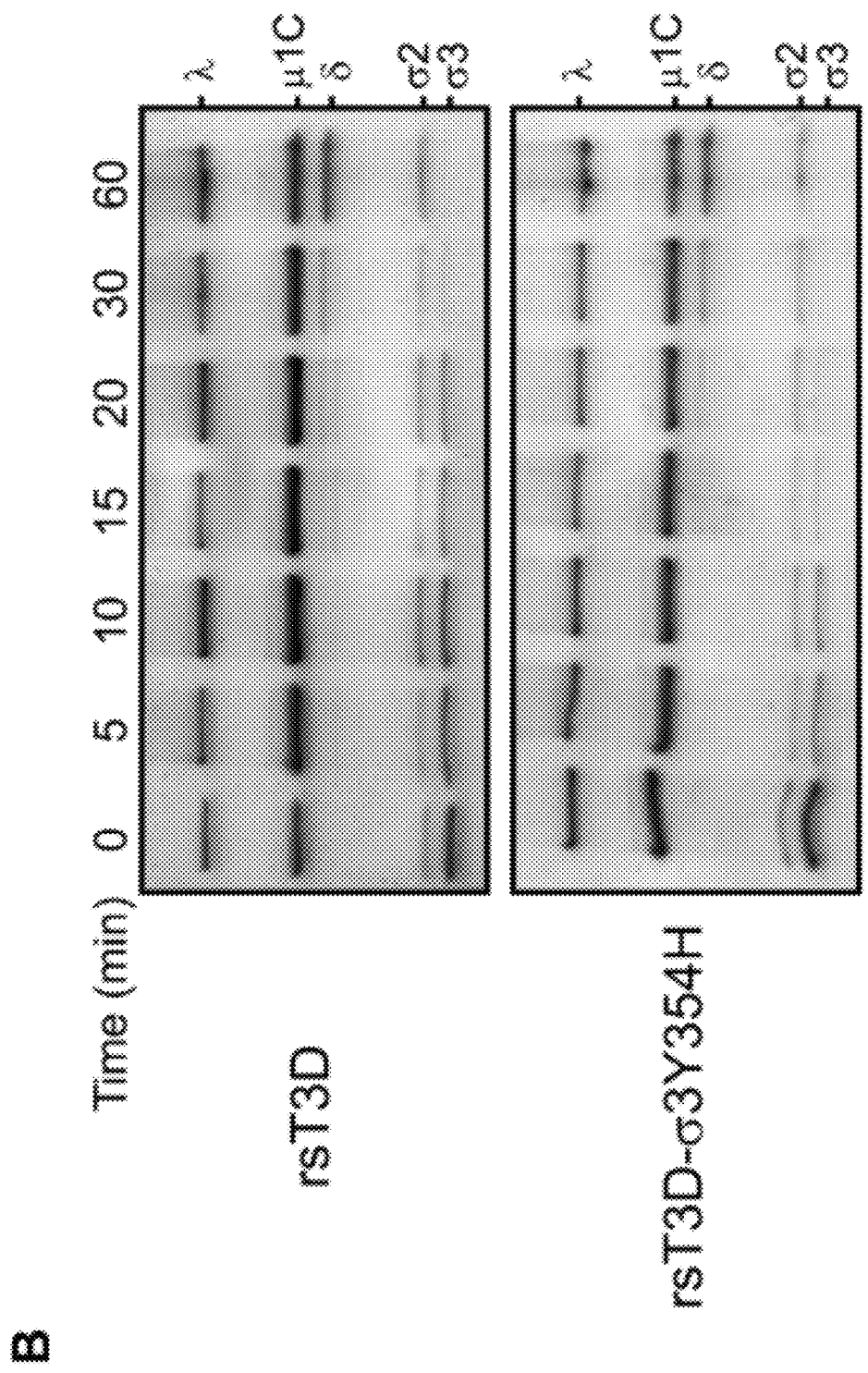
FIGS. 5A-C. A single mutation in outer-capsid protein σ3 accelerates proteolytic disassembly of reovirus.
Figure 5:
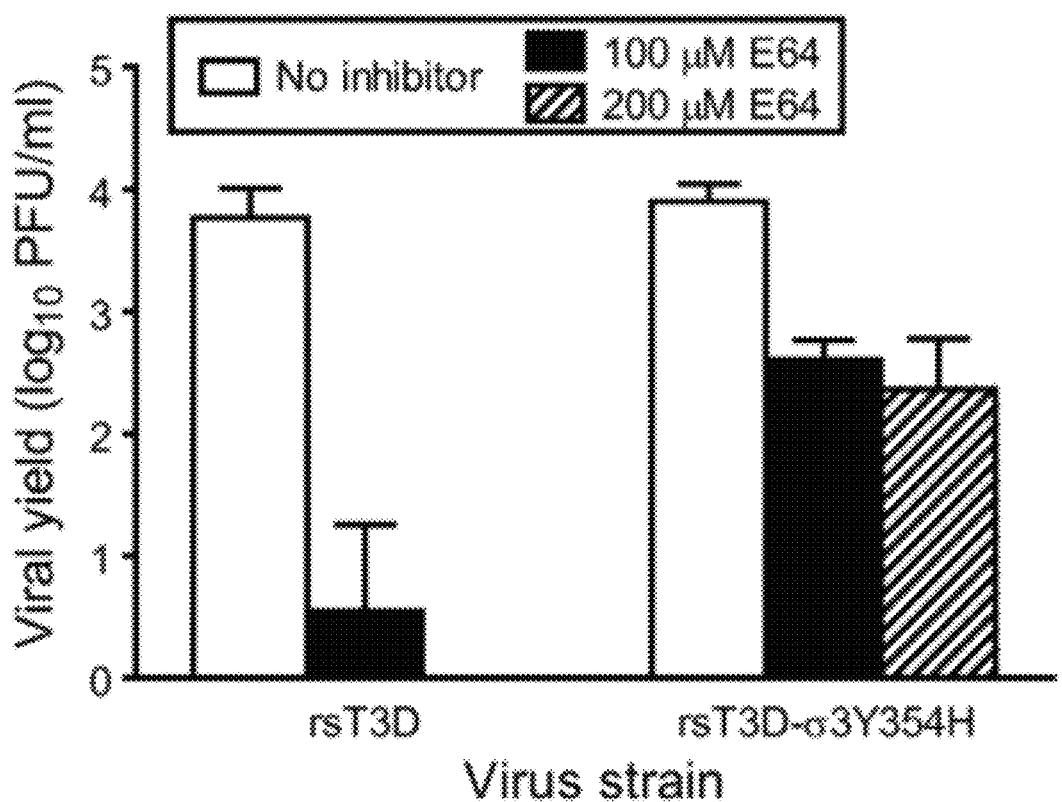

Regulation of reovirus disassembly by a single polymorphism in outer-capsid protein σ3. Previous studies identified a tyrosine-to-histidine substitution at amino acid 354 in T3D σ3 as a key regulator of the kinetics of virion-to-ISVP conversion in vitro (Wetzel et al., 1997) and viral resistance to growth inhibition by the cysteine protease inhibitor, E64 (Baer and Dermody, 1997; Ebert et al., 2001). Tyr354 is located in the virion-distal lobe of σ3 adjacent to sites in the protein that are cleaved during formation of ISVPs (Ebert et al., 2002) (FIG. 5A). The importance of this residue in viral replication has been deduced by analysis of reassortant viruses containing wt and mutant σ3 proteins and analysis of ISVPs recoated with wt and mutant forms of σ3.

To determine whether the Y354H mutation in σ3 is sufficient to confer enhanced virion-to-ISVP conversion and resistance to E64, the inventors generated rsT3D-σ3Y354H (Supplemental Table 2) and compared this virus to rsT3D for kinetics of σ3 proteolysis following protease treatment in vitro. Virions of each strain were treated with chymotrypsin for various intervals and processed for analysis of viral structural proteins by SDS-PAGE (FIG. 5B). Treatment of rsT3D and rsT3D-σ3Y354H virions with chymotrypsin resulted in degradation of σ3 and cleavage of µ1C to form δ, indicative of ISVP formation. Proteolysis of rsT3D-σ3Y354H σ3 during chymotrypsin treatment occurred with substantially faster kinetics than that of rsT3D σ3. This result indicates that amino acid 354 in σ3 protein is an independent determinant of virion susceptibility to proteolytic digestion and likely functions as an autonomous regulator of viral disassembly in cellular endosomes.

The role of σ3 mutation Y354H in virion disassembly in cyto was investigated by quantifying yields of rsT3D and rsT3D-σ3Y354H after 24 h of growth in L cells treated with 0 to 200 µM E64 (FIG. 5C). Both strains produced yields of ~1,000 fold following growth in untreated cells. However, yields of rsT3D-σ3Y354H were ~100-fold greater than those of rsT3D following growth in cells treated with 200 µM E64 (the highest concentration tested). Therefore, a single mutation in σ3, Y354H, regulates resistance of reovirus to an inhibitor of cysteine proteases within cellular endosomes.

Transduction of GFP by a recombinant reovirus. To determine whether reoviruses capable of expressing a foreign gene can be recovered following plasmid transfection, the inventors introduced sequences encoding GFP into the σ3 open-reading frame of the T3D S4 plasmid (FIG. 6A). In this configuration, GFP is expressed as a fusion protein incorporating amino acids 1-39 of σ3 protein at the N-terminus. Recombinant virus rsT3D/S4-GFP was recovered following plasmid transfection of L cells stably expressing σ3 protein. Altered mobility of the S4 gene distinguishes the electropherotypes of rsT3D and rsT3D/S4-GFP (FIG. 6B), confirming incorporation of the recombinant S4-GFP gene segment. Infection of L cells with rsT3D/S4-GFP resulted in expression of GFP and viral inclusion-forming protein µNS, but not σ3 protein (FIG. 6C). These results demonstrate that reovirus can be engineered to express foreign genes.

Example 3

Discussion

Reverse genetics technology permits testing of tightly focused, rational hypotheses about complex questions of virus structure, virus-cell interactions, and viral pathogenesis through direct engineering of the viral genome without a need to devise complicated selection strategies for isolation of viral mutants. The inventors developed a fully plasmid-based reverse genetics technology for mammalian reoviruses. This system permits selective introduction of desired mutations into cloned cDNAs encoding each of the 10 viral gene segments, followed by isolation of mutant viruses from cells transfected with the plasmid constructs. Moreover, gene segment cDNAs can be manipulated to facilitate expression of a transgene. Importantly, recombinant viruses are generated without a requirement for helper virus and free of any selection. Thus, this new technique provides a means to directly and precisely engineer the viral genome in the context of infectious virus.

The inventors used the newly developed plasmid-based reovirus reverse genetics system to engineer mutations in the σ1 and σ3 proteins. These proteins form part of the viral outer capsid, which is responsible for numerous major events in reovirus interaction with the cell and host, including attachment, disassembly within endosomes, penetration of cell membranes, induction of apoptosis, growth in the intestine and dissemination, pathways of spread, neurovirulence, and tropism within the CNS (for reviews, see. Chandran and Nibert, 2003; O'Donnell et al., 2003; Guglielmi et al., 2006). Therefore, the inventors initially applied reverse genetics technology to the study of outer-capsid proteins to better understand how these proteins mediate critical steps in reovirus replication and disease.

The infectivity of ISVPs of reovirus strain T1L in L cells is approximately 10-fold greater than that of T3D ISVPs (Nibert et al., 1995). This difference in infectivity is hypothesized to be a direct result of σ1 cleavage (Nibert et al., 1995; Chappell et al., 1998), presumably due to removal of the JAM-A-binding region of the protein. Although the T249I substitution in expressed T3D σ1 renders it resistant to cleavage by trypsin (Chappell et al., 1998), until now it has not been possible to define the role of σ1 cleavage in T3D infectivity for lack of means to generate a mutant T3D virus with the T249I change. This virus has been generated using reverse genetics, and our findings indicate that cleavage susceptibility of viral attachment protein σ1 due to a single polymorphism at amino acid position 249 is the basis for reduced infectivity of T3D ISVPs relative to virions (FIG. 3C) and contributes to diminished growth of T3D in the murine intestine following PO inoculation (FIG. 4A).

Previous studies of T3D-derived reovirus strains with altered disassembly kinetics point to a critical role for sequences in the virion-distal, C-terminal lobe of σ3 in susceptibility to acid-dependent proteolysis. A C-terminal Y354H mutation in σ3 protein of strain T3D was selected during persistent reovirus infection of L cells (PI viruses)

(Wetzel et al., 1997) and by serial passage of virus in L cells treated with E64 (D-EA viruses) (Ebert et al., 2001) or ammonium chloride (ACA-D viruses) (Clark et al., 2006). Using reovirus reverse genetics, the Y354H substitution was introduced into a wt T3D genetic background, and the resultant virus, rsT3D-σ3Y354H, demonstrated accelerated kinetics of σ3 cleavage and diminished sensitivity to the growth-inhibitory effects of E64 (FIGS. 5A-B). Residue 354 is located in a position thought to be important for controlling access to protease-hypersensitive regions in σ3, residues 208-214 and 238-242, thereby influencing σ3 cleavage kinetics (Jané-Valbuena et al., 2002). Therefore, it appears that position 354 in σ3 is a gatekeeper for the viral outer capsid, serving to regulate the balance between viral stability and an irreversible, proteolytically triggered disassembly cascade committing the virion particle to either replication or inactivation.

The inventors exploited the reovirus reverse genetics system to develop a gene delivery vehicle by replacing the σ3 open-reading frame in the S4 plasmid with a GFP-encoding cDNA, and the resultant virus, rsT3D/S4GFP, expresses GFP (FIG. 6C). The inventors see potential use for reovirus-mediated gene transduction principally in three arenas. First, genetically engineered reoviruses are excellent candidates for development of a multifunctional vaccine modality to elicit mucosal immunity. This is a very appealing idea since reovirus undergoes primary replication in intestinal tissue with few or no symptoms in humans (Tai et al., 2005). Secondly, reoviruses generated through reverse-genetics methods may serve as potent oncolytics. Reoviruses have been used for selective lysis of several different tumor cell types in vitro and in experimental animals (Coffey et al., 1998; Hirasawa et al., 2002), and wt reoviruses have shown efficacy as a virotherapeutic for aggressive and refractory human tumors, such as glioblastoma (Wilcox et al., 2001). Reverse genetics should permit the generation of a library of highly oncotropic viruses capable of targeting a wide array of tumor types in vivo with minimal risk to normal cells and tissues. Furthermore, it may be feasible to engineer reoviruses with genes that are directly tumoricidal or sensitizing to the action of conventional antineoplastic drugs. Finally, reovirus reverse genetics allows dsRNA viruses to be developed as transfection vectors for high-level expression of foreign proteins in animal cells. Expression of reovirus genes is extraordinarily efficient in infected cells, overcoming cellular antiviral responses that result in cessation of host-cell protein synthesis (Smith et al., 2006). Reoviruses also exhibit broad cell and tissue tropism, replicating to high titers in most cell types and thus may provide a useful alternative to currently available virus-based gene-transfer systems. Ideal reovirus vectors will contain stable σ1 proteins and combine excellent extracellular stability with highly efficient intracellular disassembly. The inventors find that each of these parameters can be independently adjusted through strategic alterations in outer-capsid proteins. Manipulation of inner-capsid proteins and the genomic RNA itself should allow construction of viruses able to circumvent other aspects of virus-cell and virus-host interactions that pose potential barriers to antigen and gene delivery by reoviruses. The inventors believe that this reverse genetics system is readily extrapolated to other Reoviridae family members.

Example 4

Improved System

The inventors have described, above, an entirely plasmid-based reverse genetics system for the mammalian reoviruses in which infectious virion particles can be produced using cloned cDNAs representing the 10 viral gene segments (1). Furthermore, they demonstrated that nonviral nucleic acid sequences can be inserted into the reovirus genome by generating a GFP-expressing recombinant virus. These results provide proof of principle that reovirus can be used as a delivery vehicle for foreign genes and support its further development as a vaccine vector, oncolytic, and novel transduction system for primary and transformed cells.

Figure 8:
FIG. 8. Kinetics of virus production following plasmid transfection of L cells. Cells were cotransfected with six plasmids (as illustrated in FIGS. 7A-B) or 10 plasmids (each encoding a single viral gene segment 1) representing the complete reovirus genome, and viral titers in cotransfection lysates were determined using plaque assay at the intervals shown. Results represent the means of three independent experiments. Error bars indicate S.D.

The inventors have extended this technology to enhance its manipulability, utility, and efficacy for clinical and research purposes. Specifically, they generated di- and tri-cistronic marker-rescue plasmids that co-express S1 and M1 RNAs, M2 and M3 RNAs, and S2, S3, and S4 RNAs, thus reducing from 10 to six the total number of plasmids required to rescue infectious reovirus virion particles (FIGS. 7A-B). The host vector for these new constructs is p3E5EGFP (2), which also was used in the original system to express all viral RNAs except S1. Viral cDNAs were inserted between sequences encoding the bacteriophage T7 RNA polymerase promoter and hepatitis delta virus ribozyme, as described previously (1). The anticipated nascent transcription products in cells infected with replication-defective vaccinia virus DIs-T7pol, which produces high levels of T7 RNA polymerase, are full-length reovirus (+)-strand RNAs containing native 5' termini and ribozyme sequences fused to the 3' termini. Subsequent autocatalytic removal of ribozyme sequences is expected to yield natural reovirus 3' ends. When L cells were infected with DIs-T7pol and subsequently cotransfected with the six plasmids collectively encoding the entire reovirus genome, the kinetics and total yields of virus production approximated that obtained using the original 10 plasmids (FIG. 8).

Compared to the 10-plasmid marker rescue system, the six-plasmid format requires less time and expense for reagent preparation. Thus, the six-plasmid system is more convenient and cost-effective than the 10-plasmid procedure, yet without detectable sacrifice in rescue efficiency, which represents a significant technical advancement that improves on the system's potential applications to the prevention, treatment, and mechanistic understanding of numerous diseases.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

IX. REFERENCES

The following references, to the extent that they provide exemplary procedural or other details supplementary to those set forth herein, are specifically incorporated herein by reference:

U.S. Pat. No. 4,683,202
U.S. Pat. No. 4,684,611
U.S. Pat. No. 4,952,500
U.S. Pat. No. 5,302,523

U.S. Pat. No. 5,322,783
U.S. Pat. No. 5,359,046
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Pat. No. 6,110,461
U.S. Pat. No. 6,136,307
U.S. Pat. No. 6,703,232
Almazan et al., *Proc. Natl. Acad. Sci. USA*, 97:5516-5521, 2000.
Almendro et al., *J. Immunol.*, 157(12):5411-5421, 1996.
Arap et al., *Cancer Res.*, 55(6):1351-1354, 1995.
Armstrong et al., *Virology*, 138:37, 1984.
Ausubel et al., In: *Current Protocols in Molecular Biology*, John, Wiley & Sons, Inc, NY, 1994
Baer and Dermody, *J. Virol.*, 71:4921-4928, 1997.
Barton et al., *Cell*, 104:441-451, 2001b.
Barton et al., *J. Biol. Chem.*, 276:2200-2211, 2001a.
Becker et al., *J. Virol.* 77, 5948-5963, 2003).
Bedzyk et al., *J. Biol. Chem.*, 265(30):18615-18620, 1990.
Blaney et al., *Viral Immunol.*, 19:10-32, 2006.
Bodkin et al., *J. Virol.*, 63:4676-4681, 1989.
Bodkin, and Fields, *J. Virol.*, 63:1188-1193, 1989.
Bosher and Labouesse, *Nat. Cell. Biol.*, 2:E31-E36, 2000.
Bridgen and Elliott, *Proc. Natl. Acad. Sci. USA*, 93:15400-15404, 1996.
Bussemakers et al., *Cancer Res.*, 52:2916-2922, 1992.
Caldas et al., *Cancer Res.*, 54:3568-3573, 1994.
Campbell et al., *J. Virol.*, 79:7967-7978, 2005.
Carbonelli et al., *FEMS Microbiol. Lett.*, 177(1):75-82, 1999.
Casey et al., *Oncogene*, 6(10):1791-1797, 1991.
Chandler et al., *Proc. Natl. Acad. Sci. USA*, 94(8):3596-601, 1997.
Chandran and Nibert, *Trends Microbiol.*, 11:374-382, 2003.
Chandran et al., *J. Virol.*, 75:5335-5342, 2001.
Chandran et al., *J. Virol.*, 76:9920-9933, 2002.
Chappell et al., *EMBO J.*, 21:1-11, 2002.
Chappell et al., *J. Virol.*, 71:1834-1841, 1997.
Chappell et al., *J. Virol.*, 72:8205-8213, 1998.
Chaudhary et al., *Proc. Natl. Acad. Sci. USA*, 87(3):1066-1070, 1990.
Chen and Okayama, *Mol. Cell Biol.*, 7(8):2745-2752, 1987.
Cheng et al., *Cancer Res.*, 54(21):5547-5551, 1994.
Cheung et al., *Biochem. J*, 295:427-435, 1993.
Clark et al., *J. Virol.*, 80:671-681, 2006.
Cocea, *Biotechniques*, 23(5):814-816, 1997.
Coffey et al., *Science*, 282:1332-1334, 1998.
Coley et al., *J. Virol.*, 79:3097-3106, 2005.
Collins et al., *Proc. Natl. Acad. Sci. USA*, 92:11563-11567, 1995.
Connolly et al., *J. Virol.*, 74:2981-2989, 2000.
Ebert et al., *J. Biol. Chem.*, 277:24609-24617, 2002.
Ebert et al., *J. Virol.*, 75:3197-3206, 2001.
Edelman and Crossin, *Annu. Rev. Biochem.*, 60:155-190, 1991
Edelman, *Annu. Rev. Biochem.*, 54:135-169, 1985.
Ehrlich et al., *Cell*, 118:591-605, 2004.
Fechheimer, et al., *Proc Natl. Acad. Sci. USA*, 84:8463-8467, 1987.
Fields et al., *J. Mol. Med.*, 74:673-683, 1996.
Fields, *Virology*, 46:142-148, 1971.
Fire et al., *Nature*, 391(6669):806-811, 1998.
Fodor et al., *J. Virol.*, 73:9679-9682, 1999.
Fraley et al., *Proc. Natl. Acad. Sci. USA*, 76:3348-3352, 1979.
Fraser et al., *J. Virol.*, 64:2990-3000, 1990.
Frixen et al., *J. Cell. Biol.*, 113(1):173-185, 1991.
Furlong et al., *J. Virol.*, 62:246-256, 1988.
Garcin et al., *EMBO J.*, 14:6087-6094, 1995.
Gentsch and Pacitti, *J. Virol.*, 56:356, 1985.
Giancotti and Ruoslahti, *Cell* 60(5):849-859, 1990.
Gopal, *Mol. Cell Biol.*, 5:1188-1190, 1985.
Graham and Van Der Eb, *Virology*, 52:456-467, 1973.
Grishok et al., *Science*, 287:2494-2497, 2000.
Gritsun and Gould, *Virology*, 214:611-o18, 1995.
Guglielmi et al., *Curr. Top. Microbiol. Immunol.*, 309:1-38, 2006.
Harland and Weintraub, *J. Cell Biol.*, 101(3):1094-1099, 1985.
Hirasawa et al., *Cancer Res.*, 62:1696-1701, 2002.
Hollstein et al., *Science*, 253(5015):49-53, 1991.
Horimoto and Kawaoka, *Trends Mol. Med.*, 12:506-514, 2006.
Hussussian et al., *Nat. Genet.*, 8(1):15-21, 1994.
Ishii et al., *Virology*, 302:433-444, 2002.
Jackson and Muldoon, *J. Infect. Dis.*, 128:811, 1973.
Jane-Valbuena et al., *J. Virol.*, 76:5184-5197, 2002.
Kaeppler et al., *Plant Cell Reports*, 9:415-418, 1990.
Kamb et al., *Science*, 2674:436-440, 1994.
Kaneda et al., *Science*, 243:375-378, 1989.
Kato et al, *J. Biol. Chem.*, 266:3361-3364, 1991.
Ketting et al., *Cell*, 99(2):133-141, 1999.
Kinney et al., *Virology*, 230:300-308, 1997.
Komoto et al., *Proc. Natl. Acad. Sci. USA*, 103:4646-4651, 2006.
Kraus et al. *FEBS Lett.*, 428(3):165-170, 1998.
Lareyre et al., *I Biol. Chem.*, 274(12):8282-8290, 1999.
Lawson et al., *Proc. Natl. Acad. Sci. USA*, 92:4477-4481, 1995.
Lee et al., *Biochem. Biophys. Res. Commun.*, 238(2):462-467, 1997.
Levenson et al., *Hum. Gene Ther.*, 9(8):1233-1236, 1998.
Lin and Avery, *Nature*, 402:128-129, 1999.
Lin and Guidotti, *J. Biol. Chem.*, 264:14408-14414, 1989.
Liu et al., *J. Cell Sci.*, 113:2363-2374, 2000.
Macejak and Sarnow, *Nature*, 353:90-94, 1991.
Maginnis et al., *J. Virol.*, 80:2760-2770, 2006.
Maniatis, et al., *Molecular Cloning, A Laboratory Manual*, Cold Spring Harbor Press, Cold Spring Harbor, N.Y., 1988.
Martin-Padura et al., *J. Cell Biol.*, 142:117-127, 1998.
Matsura et al., *Biochim. Biophys. Acta*, 1123(3):309-315, 1992.
Montgomery et al., *Proc. Natl. Acad. Sci. USA*, 95:15502-15507, 1998.
Mori et al., *Cancer Res.*, 54(13):3396-3397, 1994.
Nabel et al., *Science*, 244(4910):1342-1344, 1989.
Neumann et al., *Proc. Natl. Acad. Sci. USA*, 96:9345-9350, 1999.

Neutra, *J. Infect. Dis.,* 179:Suppl 3:S441-3, 1999.
Nibert and Schiff, In: *Reoviruses and their replication,* Fields Virology, Knipe and Howley (Eds.), Philadelphia, Lippincott Williams & Wilkins, pp. 1679-1728, 2001.
Nibert et al., *J. Virol.,* 69:5057-5067, 1999.
Nicolau and Sene, *Biochim. Biophys. Acta,* 721:185-190, 1982.
Nicolau et al., *Methods Enzymol.,* 149:157-176, 1987.
Niwa et al., *Gene* 108, 193-199, 1991.
Nobori et al., *Nature* (London), 368:753-756, 1995.
Nomoto et al., *Gene,* 236(2):259-271, 1999.
Obrink, *Bioessays,* 13(5):227-234, 1991.
Odegard et al., *J. Virol.,* 78:8732-8745, 2004.
Odin and Obrink, *Exp. Cell Res.,* 171(1):1-15, 1987.
O'Donnell et al., *Int. Rev. Immunol.,* 22:477-503, 2003.
O'Donnell et al., *J. Clin. Invest.,* 115:2341-2350, 2005.
O'Donnell et al., *J. Virol.,* 80:1077-1086, 2006.
Okamoto et al., *Proc. Natl. Acad. Sci. USA,* 91(23):11045-11049, 1994.
Olland et al., *EMBO J.,* 20:979-989, 2001.
Omirulleh et al., *Plant Mol. Biol.,* 21(3):415-428, 1993.
Orlow et al., *Cancer Res,* 54(11):2848-2851, 1994.
Parker et al., *J. Virol.,* 76:4483-4496, 2002.
Paul et al. *Virology,* 172:382-385, 1989.
PCT Appln. WO 95/06128
PCT Appln. WO 94/09699
Pelletier and Sonenberg, *Nature,* 334(σ180):320-325, 1988.
Plasterk and Ketting, *Curr. Opin. Genet. Dev.,* 10:562-567, 2000.
Potrykus et al., *Mol. Gen. Genet.,* 199(2):169-177, 1985.
Potter et al., *Proc. Natl. Acad. Sci. USA,* 81:7161-7165, 1984.
Racaniello and Baltimore, *Science,* 214:916-919, 1981.
Rice et al., *New Biol.,* 1:285-296, 1989.
Riezebos-Brilman et al., *J. Clin. Virol.,* 35:233-243, 2006.
Rippe, et al., *Mol. Cell Biol.,* 10:689-695, 1990.
Roner et al., *Proc. Natl. Acad. Sci. USA,* 94:6826-6830, 1997.
Roner & Steele, *Virology* 5:358(1):89-97, 2007 (epub September 2006).
Rubin and Fields, *J. Exp. Med.,* 152:853-868, 1980.
Rubin et al., *J. Clin. Invest.,* 90:2536-2542, 1992.
Sabin, *Science,* 130:1387-1389, 1959.
Sambrook and Russell, Molecular Cloning: A Laboratory Manual 3$^{rd}$ Ed., Cold Spring Harbor Laboratory Press, 2001.
Schneider et al., *Proc. Natl. Acad. Sci. USA,* 102:3441-3446, 2005.
Schnell et al., *EMBO J.,* 13:4195-4203, 1994.
Serrano et al., *Nature,* 366:704-707, 1993.
Serrano et al., *Science,* 267(5195):249-252, 1995.
Sharp and Zamore, *Science,* 287:2431-2433, 2000.
Sharp, *Genes Dev.,* 13:139-141, 1999.
Silverstein and Schur, *Virology,* 41:564-566, 1970.
Smith et al., *J. Virol.,* 80:2019-2033, 2006.
Stanley, In: *Comparative Diagnosis of Viral Diseases,* 385-421, Academic Press, NY, 1974.
Stoeckel and Hay, *Curr. Opin. Mol. Ther.,* 8:249-260, 2006.
Tabara et al., *Cell,* 99(2):123-132, 1999.
Tai et al., *J. Infect. Dis.,* 191:1221-1224, 2005.
Takahasi and Sawasaki, *In Vitro Cell Dev. Biol.,* 28A(6):380-382, 1992.
Tsumaki et al., *J. Biol. Chem.,* 273(36):22861-22864, 1998.
Tur-Kaspa et al., *Mol. Cell Biol.,* 6:716-718, 1986.
Tyler et al., *Neurology,* 35:88-92, 1985.
Umbas et al., *Cancer Res.,* 52:5104-5109, 1992.
Virgin et al., *J. Virol.,* 62:4594-4604, 1988.
Watanabe et al., *J. Virol.,* 78:999-1005, 2004.
Weinberg, *Science,* 254(5035):1138-1146, 1991.
Wetzel et al., *J. Virol.,* 71:1362-1369, 1997.
Whelan et al., *Proc. Natl. Acad. Sci. USA,* 92:8388-8392, 1995.
Wiener and Joklik, *Virology,* 169:194-203, 1989
Wilcox et al., *J. Natl. Cancer Inst.,* 93:903-912, 2001.
Wilson et al., *J. Virol.,* 70:6598-6606, 1996.
Wilson et al., *Science,* 244:1344-1346, 1989.
Wong et al., *Gene,* 10:87-94, 1980.
Wu and Wu, *Biochemistry,* 27: 887-892, 1988.
Wu and Wu, *J. Biol. Chem.,* 262:4429-4432, 1987.
Wu et al., *Biochem. Biophys. Res. Commun.,* 233(1):221-226, 1997.
Yoneda et al., *Proc. Natl. Acad. Sci. USA,* 103:16508-16513, 2006.
Yount et al., *Proc. Natl. Acad. Sci. USA,* 100:12995-13000, 2003.
Yun et al., *J. Virol.,* 77:6450-6465, 2003.
Zhao-Emonet et al., *Biochim. Biophys. Acta,* 1442(2-3):109-119, 1998.

What is claimed is:

1. A method of generating an infectious Reoviridae particle comprising:

(a) providing cDNAs corresponding to each viral RNA transcript, each of said cDNAs being under the control of an RNA polymerase promoter;

(b) transferring each of said cDNAs into a host cell that expresses said RNA polymerase that directs transcription from said promoter; and (c) culturing said host cell under conditions supporting production of a Reoviridae particle.

2. The method of claim 1, further comprising isolating said Reoviridae particle.

3. The method of claim 1, wherein said Reoviridae particle is from the genus Orthoreovirus, Orbivirus, Rotavirus, Coltivirus, Seadornavirus, Aquareovirus, Cypovirus, Fijivirus, Phytoreovirus, Oryzavirus, or Mycoreovirus.

4. The method of claim 1, wherein said Reoviridae particle is a reovirus particle, and said RNA polymerase is a bacteriophage T7 RNA polymerase.

5. The method of claim 1, wherein said host cell comprises a genomic DNA sequence expressing said RNA polymerase.

6. The method of claim 1, wherein said host cell comprises an episomal nucleic acid sequence expressing said RNA polymerase.

7. The method of claim 6, wherein said episomal nucleic acid sequence is a viral expression construct.

8. The method of claim 7, wherein said viral expression construct is a vaccinia viral expression construct.

9. The method of claim 1, wherein said host cell is a 293T cell, 3T3 cell, Chinese hamster ovary cell, HeLa cell, L929 cell, murine embryonic fibroblast cell, murine erythroleukemia cell, Vero cell, CV-1 cell, or HT1080 cell.

10. The method of claim 1, wherein step (b) comprises lipofection, calcium phosphate precipitation, electroporation, or nucleofection.

11. The method of claim 1, wherein said cDNAs are comprised within plasmids.

12. The method of claim 1, wherein multiple cDNAs are under the control of a single promoter.

13. The method of claim 12, wherein said multiple cDNAs are separated by internal ribosome entry sites.

14. The method of claim 12, wherein 2, 3 or 4 cDNAs are under the control of a single promoter.

15. The method of claim 12, wherein all of said cDNAs are comprised in 6, 7, 8, 9 or 10 plasmids.

16. The method of claim 1, wherein 2, 3 or 4 cDNAs are under the control of multiple promoters.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial
<220> FEATURE:
<223> OTHER INFORMATION: Synthetic primer

<400> SEQUENCE: 1
attcaaagga attacgta                                                     18

<210> SEQ ID NO 2
<211> LENGTH: 18
<212> TYPE: DNA
<213> ORGANISM: Artificial
<220> FEATURE:
<223> OTHER INFORMATION: Synthetic primer
```

-continued

```
<400> SEQUENCE: 2
attcaaagaa attacgta                                                    18

<210> SEQ ID NO 3
<211> LENGTH: 18
<212> TYPE: DNA
<213> ORGANISM: Artificial
<220> FEATURE:
<223> OTHER INFORMATION: Synthetic primer

<400> SEQUENCE: 3
attcaaagaa attacgta                                                    18

<210> SEQ ID NO 4
<211> LENGTH: 6
<212> TYPE: PRT
<213> ORGANISM: Artificial
<220> FEATURE:
<223> OTHER INFORMATION: Synthetic peptide

<400> SEQUENCE: 4

Ile Gln Arg Asn Tyr Val
1               5
```